United States Patent
Yusa et al.

(10) Patent No.: US 12,378,650 B2
(45) Date of Patent: *Aug. 5, 2025

(54) METAL MATERIAL AND ARTICLES MADE THEREFROM HAVING BIOLOGICAL PROPERTIES

(71) Applicant: KOMATSUSEIKI KOSAKUSHO CO., LTD., Suwa (JP)

(72) Inventors: Fumie Yusa, Ikoma (JP); Thomas J. Webster, Barrington, RI (US); Takafumi Komatsu, Suwa (JP)

(73) Assignee: KOMATSUSEIKI KOSAKUSHO CO., LTD, Nagano (JP)

( * ) Notice: Subject to any disclaimer, the term of this patent is extended or adjusted under 35 U.S.C. 154(b) by 988 days.

This patent is subject to a terminal disclaimer.

(21) Appl. No.: 17/289,960

(22) PCT Filed: Mar. 20, 2020

(86) PCT No.: PCT/IB2020/000135
§ 371 (c)(1),
(2) Date: Apr. 29, 2021

(87) PCT Pub. No.: WO2020/194045
PCT Pub. Date: Oct. 1, 2020

(65) Prior Publication Data
US 2022/0010417 A1    Jan. 13, 2022

Related U.S. Application Data

(60) Provisional application No. 62/822,134, filed on Mar. 22, 2019.

(51) Int. Cl.
*C22C 38/44*    (2006.01)
*C21D 9/46*    (2006.01)
(Continued)

(52) U.S. Cl.
CPC ............... *C22C 38/44* (2013.01); *C21D 9/46* (2013.01); *C22C 38/02* (2013.01); *C22C 38/04* (2013.01); *C21D 2211/001* (2013.01)

(58) Field of Classification Search
CPC ......... C22C 38/44; C22C 38/02; C22C 38/04; C22C 38/40; C21D 9/46; C21D 2211/001;
(Continued)

(56) References Cited

U.S. PATENT DOCUMENTS

2003/0083731 A1    5/2003  Kramer
2012/0141562 A1*   6/2012  Achneck ............... A61L 27/06
                                                    424/93.21
(Continued)

FOREIGN PATENT DOCUMENTS

CN    108531817 A    9/2018
EP    0 992 599 A1   4/2000
(Continued)

OTHER PUBLICATIONS

Yu et al., Surface Nanocrystallization for Bacterial Control, Langmuir article, 2010 American Chemical Society (Year: 2010).*
(Continued)

*Primary Examiner* — Danielle M. Carda
(74) *Attorney, Agent, or Firm* — WHDA, LLP

(57) ABSTRACT

The invention relate to a metal material and article made from the metal material having biological properties, such as antibiotic properties, including a stainless steel metal material comprising a homogeneous crystal grain nanostructure and having an average crystal grain size from 0.1 to 3 μm configured (i) to inhibit adhesion, growth or combination thereof of microorganisms, (ii) to promote adhesion, growth or combination thereof of predetermined eukaryotic cells, or
(Continued)

(iii) to inhibit adhesion, growth or combination thereof of predetermined eukaryotic cells.

38 Claims, 18 Drawing Sheets

(51) Int. Cl.
    *C22C 38/02*     (2006.01)
    *C22C 38/04*     (2006.01)

(58) Field of Classification Search
    CPC ....... C21D 6/004; A61L 27/042; A61L 27/50; A61L 27/54; A61L 29/14; A61L 29/16; A61L 31/022; A61L 31/14; A61L 31/16; A61L 27/06; A61L 29/02; C12N 11/14
    USPC .......................................................... 420/46
    See application file for complete search history.

(56) References Cited

U.S. PATENT DOCUMENTS

| | | | |
|---|---|---|---|
| 2014/0342954 | A1 | 11/2014 | Ingber et al. |
| 2021/0298320 | A1* | 9/2021 | Komatsu ................. C12N 1/38 |
| 2022/0010417 | A1 | 1/2022 | Yusa |
| 2022/0226548 | A1* | 7/2022 | Yusa ....................... A61L 29/16 |

FOREIGN PATENT DOCUMENTS

| | | | |
|---|---|---|---|
| JP | 2000-096165 A | | 4/2000 |
| JP | 2018100449 A | * | 5/2018 |

OTHER PUBLICATIONS

Murray et al., Evaluation of Bactericidal and anti-biofilm properties of a novel surface-active organosilane biocide against healthcare associated pathogens and Pseudomonas aeruginosa biofilm, PLOS one, Aug. 7, 2017 (Year: 2017).*
Office Action dated May 13, 2022, issued in counterpart JP application No. 2021-529351, with English translation. (11 pages).
Extended (Supplementary) European Search Report dated Apr. 8, 2022, issued in EP application No. 19867194.3 (counterpart to U.S. Appl. No. 17/273,807). (10 pages).
Sreekumari et al., "Bacterial attachment to stainless steel welds: Significance of substratum microstructure", Biofouling: The Journal of Bioadhesion and Biofilm Research, 2001, vol. 17, No. 4, pp. 303-316, cited in EP Extended European Search Report dated Apr. 8, 2022. (15 pages).
Truong et al., "Effect of ultrafine-grained titanium surfaces on adhesion of bacteria", Applied Microbiology and Biotechnology, 2009, vol. 83, No. 5, pp. 925-937, cited in EP Extended European Search Report dated Apr. 8, 2022. (13 pages).
Notification Concerning Transmittal of Copy of International Preliminary Report on Patentability (Form PCT/IB/326) issued in counterpart International Application No. PCT/IB2020/000135 mailed Oct. 7, 2021 with Forms PCT/IB/373 and PCT/ISA/237. (6 pages).
Office Action dated Feb. 22, 2022, issued in JP Application No. 2021-510672, with English Translation. (Issued in counterpart U.S. Appl. No. 17/273,807) (12 pages).
Office Action dated Mar. 8, 2022, issued in AU Application No. 2019346107, with English Translation. (Issued in counterpart U.S. Appl. No. 17/273,807) (3 pages).
Office Action dated Mar. 10, 2022, issued in counterpart AU Application No. 2020245240, with English Translation. (4 pages).
Office Action dated Oct. 18, 2022, issued in counterpart JP application No. 2021-529351, with English translation(8 pages).
Office Action dated Oct. 27, 2022, issued in JP application No. 2021-510672, with English translation (counterpart to U.S. Appl. No. 17/273,807). (12 pages).

International Search Report dated Jul. 14, 2020, issued in counterpart International Application No. PCT/IB2020/000135. (3 pages).
Bassous et al., "3-D Printed Ti-6A1-4V scaffolds for supporting osteoblast and restricting bacterial functions without using drugs: Predictive equations and experiments", Acta Biomaterialia, 96 (2019), pp. 662-673. (12 pages).
Liu et al., "Understanding the Role of Polymer Surface Nanoscale Topography on Inhibiting Bacteria Adhesion and Growth", ACS Biomaterials Science & Engineering, (2016), 2, pp. 122-130. Cited in Specification. (4 pages).
Yu et al., "Surface Nanocrystallization for Bacterial Control", Langmuir, (2010), vol. 26, pp. 10930-10934. Cited in ISR. (5 pages).
Bagherifard et al., "The influence of nanostructured features on bacterial adhesion and bone cell functions on severely shot peened 316L stainless steel", Biomaterials, Sep. 12, 2015, vol. 73, pp. 185-197. Cited in ISR. (13 pages).
Gunay-Bulutsuz et al., "Biological responses of ultrafine grained pure titanium and their sand blasted surfaces", Materials Science & Engineering C, May 18, 2018, vol. 91, pp. 382-388. Cited in ISR. (7 pages).
Tufan et al. "Efficient fabrication of ultrafine-grained 316L stainless steel surfaces for orthopaedic applications", Materials Science and Technology, 2019. 08. 25, vol. 35, pp. 1891-1897. Cited in ISR. (7 pages).
Gong et al., "On the mechanical behavior of austenitic stainless steel with nano/ultrafine grains and comparision with micrometer austenitic grains counterpart and their biological functions", Journal of the Mechanical Behavior of Biomedical Materials, Sep. 14, 2019, vol. 101, 103433. Cited in ISR. (7 pages).
Supplementary European Search Report dated Aug. 29, 2022, issued in counterpart EP application No. 20 77 9234.2 (10 pages).
Sreekumari, Kurissery R et al., "Bacterial attachment to stainless steel welds: Significance of substratum microstructure", Biofouling: The Journal of Bioadhesion and Biofilm research, vol. 17, No. 4, Dec. 1, 2002 (Dec. 1, 2001), pp. 303-316, XP055855134, GN ISSN: 0892-7014, DOI: 10.1080/08927010109378490 Retrieved from the Internet: <URL:https://www.tandfonline.com/doi/pdf/10.1080/08927010109378490?needAccess=true *the* whole document*.
Examination Report dated Oct. 10, 2022, issued in AU application No. 2019346107 (counterpart to U.S. Appl. No. 17/273,807). (6 pages).
Examination Report dated Oct. 10, 2022, issued in counterpart AU application No. 2020245240. (5 pages).
Song et al., "Overview of processing, microstructure and mechanical properties of ultrafine grained bcc steels", Materials Science & Engineering A, 2006, vol. 441, No. 1-2, pp. 1-17, cited in both IN Office Actions dated Oct. 10, 2022. (17 pages).
Decision of Dismissal of Amendment dated May 18, 2023, issued in counterpart to JP Application No. 2021-510672, with English translation. (9 pages).
International Search Report dated Feb. 25, 2020, issued in application No. PCT/IB2019/001041, (counterpart to U.S. Appl. No. 17/273,807) (3 pages).
Notification Concerning Transmittal of International Preliminary Report on Patentability (Forms PCT/IB/326) issued in International Application No. PCT/IB2019/001041 mailed Apr. 8, 2021 with Forms PCT/IB/373 and PCT/ISA/237. (counterpart to U.S. Appl. No. 17/273,807) (8 pages).
Bin Yu, et al., "Surface Nanocrystallization for Bacterial Control," Langmuir, 2010 26 (13), pp. 10930-10934 (hereafter. "Yu") (Year 2010), (counterpart to U.S. Appl. No. 17/273,807) (5 pages).
Jang et al., "Inhibition of Bacterial Adhesion on Nanotextured Stainless Steel 316L by Electrochemical Etching." ACS Biomater. Sci. Eng. 2018, 4, pp. 90-97. (Published Dec. 12, 2017) (Year: 2017), (counterpart to U.S. Appl. No. 17/273,807) (8 pages).
Final Office Action dated Sep. 27, 2024, issued in U.S. Appl. No. 17/273,807. (22 pages).
Sharma, S. et al., "Subnanometric Roughness Affects the Deposition and Mobile Adhesion of *Escherichia coli* on Silanized Glass Surfaces," Langmuir, 2016, 32, pp. 5422-5433; Cited in U.S. Final Office Action dated Sep. 27, 2024. (12 pages).

(56) References Cited

OTHER PUBLICATIONS

Frost, F. et al., "Sub-nanometer Smoothing of Diamond-turned Metal Surfaces using Ion Beams," Towards Synthesis of Micro-/Nano-systems, The 11th International Conference on Precision Engineering, Aug. 16-18, 2006, JSPE Publication Series No. 5, pp. 239-242; Cited in U.S. Final Office Action dated Sep. 27, 2024. (5 pages).

\* cited by examiner

FIG. 4C

| Grain size (μm) | Sample | viability (%) Day 3 |
|---|---|---|
| 0.23 | UFGSS SUS 304 8.04mm$^2$ | 92.88 |
| 15 | CG SUS 304 8.04mm$^2$ | 88.67 |
| 0.22 | UFGSS SUS 304 16.21mm$^2$ | 102.55 |
| 12 | CG SUS 304 16.21mm$^2$ | 92.89 |
| 0.27 | UFGSS SUS 304 32.92mm$^2$ | 108.56 |
| 21.5 | CG SUS 304 32.92mm$^2$ | 96.81 |

FIG. 5C

| Grain size (μm) | Sample | viability (%) Day 3 |
|---|---|---|
| 0.18 | UFGSS SUS 316 8.04mm$^2$ | 95.09 |
| 7.1 | CG SUS 316 8.04mm$^2$ | 91.80 |
| 0.22 | UFGSS SUS 316 16.21mm$^2$ | 89.53 |
| 10.7 | CG SUS 316 16.21mm$^2$ | 94.52 |
| 0.25 | UFGSS SUS 316 32.92mm$^2$ | 91.503 |
| 16.5 | CG SUS 316 32.92mm$^2$ | 101.10 |

*p<0.05 respect control 1, on day 5

**p<0.05 respect control 2, on day 5

METAL MATERIAL AND ARTICLES MADE THEREFROM HAVING BIOLOGICAL PROPERTIES

RELATED APPLICATIONS

This application claims priority to U.S. Provisional Application Ser. No. 62/822,134, filed Mar. 22, 2019, the disclosure of which is hereby incorporated herein by reference in its entirety.

FIELD

Aspects of the present disclosure relate to a metal material and metallic devices having a homogenous average crystal grain size nanostructure and biological properties.

BACKGROUND

Reports have shown that about 400,000 vascular catheter-related bacteremias and fungemias occur annually in the United States. Such infections can be life-threatening, and are generally difficult to treat. Bactericidal action to reduce or prevent colonization are typically by coating the device with antibiotics.

Alternatively, it is desirable for implantable devices, to increase or decrease adhesion and/or growth of eukaryotic cells.

SUMMARY

Aspects of the disclosure relate to metal materials and articles made therefrom having a grain size that provide a surface energy promoting antibacterial action, improvement in eukaryotic cell growth or combination thereof.

Aspects of the disclosure relate to metal materials comprising an homogenous crystal grain having an average crystal grain size from 100 nm to 3 µm, more particularly 200 nm to 1 µm and more particularly from 200 nm to 500 nm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

In some embodiments, the metal material inhibits adsorption or growth of microorganisms on the metal material by at least 50%. In some embodiments, the microorganism is a gram+bacterium. In some embodiments, the microorganism is a gram−bacterium. In some embodiments, the microorganism is one of *Staphylococcus aureus, Staphylococcus epidermidis*, Methicillin-resistant *Staphylococcus aureus* (MRSA), *E. coli*, multidrug-resistant *E. coli* (MDR), or *Pseudomonas aeruginosa*.

In some embodiments, the metal material decreases inflammatory cell adsorption or growth, decrease bacterial adsorption or growth, increase osteoblast adsorption or growth, increase endothelial cell adsorption or growth or combinations thereof.

In some embodiments, the metal material has an average crystal grain size for substantially inhibiting adsorption or growth of the microorganism which is determined from a response profile which is a result obtained by cultivating the microorganism on a metal material having crystal grains with different average crystal grain sizes and plotting a number of the microorganism after the cultivation with respect to the average crystal grain size.

In some embodiments, the crystal grain has an average crystal grain size from 0.1 µm or more to 3 µm or less. In some embodiments, the crystal grain has an average crystal grain size from 0.2 µm or more to 1 µm or less. In some embodiments, the crystal grain has an average crystal grain size from 0.2 µm or more to 0.5 µm or less. In some embodiments, the crystal grain has an average crystal grain size from 0.1 µm or more to 1 µm or less. In some embodiments, the crystal grain has an average crystal grain size from 0.2 µm or more to 0.5 µm or less.

In some embodiments, the metal material can be stainless steel. In some embodiments, the metal material can be type 304 stainless steel. In some embodiments, the metal material can be type 316 stainless steel. In some embodiments, the type 316 stainless steel is 316L stainless steel.

In some embodiments, the metal material is a wire or a rod. In some embodiments, the average crystal grain size is from 0.1 µm or more to 3 µm or less. In some embodiments, the average crystal grain size is from 0.2 µm or more to 1 µm or less. In some embodiments, the average crystal grain size is from 0.2 µm nm to 0.5 µm.

Some aspects of the disclosure relate to a medical device made from the metal material described herein.

Some aspects of the disclosure relate a foil made from the material metal described herein.

Some aspects of the disclosure relate to an instrument made from the material metal material described herein.

Some aspects of the disclosure relate to a metal wire comprising a crystal grain having an average crystal grain size from 0.2 µm to 1 µm, wherein the metal wire has antibiotic properties. In some embodiments, the average crystal grain size is from 0.2 µm to 0.5 µm.

Some aspects of the disclosure relate to comprising a metallic medical device comprising a crystal grain having an average crystal grain size from 100 nm to 3 µm, wherein the medical device has antibiotic properties. In some embodiments, the average crystal grain size is from 0.2 µm to 1 µm. In some embodiments, the average crystal grain size is from 0.2 µm to 0.5 µm.

In some embodiments, the metal material can be stainless steel. In some embodiments, the metal material can be type 304 stainless steel. In some embodiments, the metal material can be type 316 stainless steel. In some embodiments, the type 316 stainless steel is 316L stainless steel.

In some embodiments, the metallic medical device inhibits adsorption or growth of microorganisms on the metallic medical device by at least 50%.

Aspects of the disclosure relate to a stainless steel metal material and article made therefrom. Aspects of the disclosure relate to a stainless steel metal material comprising a homogeneous crystal grain nanostructure and having an average crystal grain size from 0.1 to 3 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells. In some embodiments, the stainless steel metal material comprises a homogeneous crystal grain nanostructure and having an average crystal grain size from 0.2 to 1 µm. In some embodiments, the stainless steel metal material comprises a homogeneous crystal grain nanostructure and having an average crystal grain size from 0.2 to 0.5 µm. In some embodiments, the metal material is type 304 stainless steel metal. In some embodiments, the metal material is magnetized. In some embodiments, the metal material is type 316 stainless steel metal. In some embodiments, the metal material is magnetized.

Some aspects of the disclosure relate to a type 304 stainless steel metal material comprising a homogeneous crystal grain nanostructure and having an average crystal grain size from 0.2 to 0.5 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

Some aspects of the disclosure relate to a type 316 stainless steel metal material comprising a homogeneous crystal grain nanostructure and having an average crystal grain size from 0.2 to 0.5 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

In some embodiments, the metal material inhibits adsorption or growth of microorganisms on the metal material by at least 50%.

In some embodiments, the metal material is magnetized.

In some embodiments, the metal material decreases inflammatory cell adsorption or growth, decrease bacterial adsorption or growth, increase osteoblast adsorption or growth, increase endothelial cell adsorption or growth or combinations thereof.

In some embodiments, the metal material decreases inflammatory cell adsorption or growth, decrease bacterial adsorption or growth, increase osteoblast adsorption or growth, increase endothelial cell adsorption or growth or combinations thereof.

In some embodiments, the microorganism is a gram positive bacterium. In some embodiments, the microorganism is a gram negative bacterium. In some embodiments, the microorganism is one of *Staphylococcus aureus, Staphylococcus epidermidis*, Methicillin-resistant *Staphylococcus aureus* (MRSA), *E. coli*, Multi-drug resistant *E. coli, Pseudomonas aeruginosa*.

In some embodiments, the article is a wire or a rod. In some embodiments, the article a medical device. In some embodiments, the article is a stainless steel metal material. In some embodiments, the article is an instrument. In some embodiments, the article is a kitchenware.

Some aspects of the disclosure relate to a wire or a rod made from a stainless steel metal material comprising a homogeneous crystal grain nanostructure and having an average crystal grain size from 0.2 to 0.5 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells. In some embodiments, the metal material can be type 304 stainless steel. In some embodiments, the metal material can be type 316 stainless steel. In some embodiments, the type 316 stainless steel is 316L stainless steel. In some embodiments, the metal material is 304 stainless steel metal and the material is magnetized. In some embodiments, the wire or rod wherein the metal material is type 316 stainless steel metal and the material is magnetized.

Some aspects of the disclosure relate to a medical device made from a stainless steel metal material comprising a homogeneous crystal grain nanostructure and having an average crystal grain size from 0.2 to 0.5 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells. In some embodiments, the metal material can be type 304 stainless steel. In some embodiments, the metal material can be type 316 stainless steel. In some embodiments, the type 316 stainless steel is 316L stainless steel. In some embodiments, the metal material is type 304 stainless steel metal and the material is magnetized. In some embodiments, the metal material is type 316 stainless steel metal and the material is magnetized.

Some aspects of the disclosure relate to a foil made from a stainless steel metal material comprising a homogeneous crystal grain nanostructure and having an average crystal grain size from 0.2 to 0.5 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells. In some embodiments, the metal material can be type 304 stainless steel. In some embodiments, the metal material can be type 316 stainless steel. In some embodiments, the type 316 stainless steel is 316L stainless steel. In some embodiments, the metal material is type 304 stainless steel metal and the material is magnetized. In some embodiments, the metal material is type 316 stainless steel metal and the material is magnetized.

Some aspects of the disclosure relate to an instrument made from a stainless steel metal material comprising a homogeneous crystal grain nanostructure and having an average crystal grain size from 0.2 to 0.5 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells. In some embodiments, the metal material can be type 304 stainless steel. In some embodiments, the metal material can be type 316 stainless steel. In some embodiments, the type 316 stainless steel is 316L stainless steel. In some embodiments, the metal material is type 304 stainless steel metal and the material is magnetized. In some embodiments, the metal material is type 316 stainless steel metal and the material is magnetized.

Some aspects of the disclosure relate to a stainless steel metal wire comprising a homogeneous crystal grain nanostructure and having an average crystal grain size from 0.2 to 0.5 µm, wherein the metal wire has antibiotic properties. In some embodiments, the metal material can be type 304 stainless steel. In some embodiments, the metal material can be type 316 stainless steel. In some embodiments, the type 316 stainless steel is 316L stainless steel. In some embodiments, the metal material is type 304 stainless steel metal and the material is magnetized. In some embodiments, the metal material is type 316 stainless steel metal and the material is magnetized.

Some aspects of the disclosure relate to a stainless steel medical device comprising a homogeneous crystal grain nanostructure and having an average crystal grain size from 0.2 to 0.5 µm, wherein the medical device has antibiotic properties. In some embodiments, the metal material can be type 304 stainless steel. In some embodiments, the metal material can be type 316 stainless steel. In some embodiments, the type 316 stainless steel is 316L stainless steel. In some embodiments, the metal material is type 304 stainless steel metal and the material is magnetized. In some embodiments, the metal material is type 316 stainless steel metal and the material is magnetized. In some embodiments, the medical device inhibits adsorption or growth of microorganisms on the medical device by at least 50%.

BRIEF DESCRIPTION OF THE DRAWINGS

FIGS. 4A-4C show the percent viability of the human dermal fibroblast when grown on type 304 stainless steel metal samples with different grain sizes according to some embodiments.

FIGS. 5A-5C show the percent viability of the human dermal fibroblast when grown on type 316 stainless steel metal samples with different grain sizes according to some embodiments.

FIG. 12A is a response profile obtained by plotting a response amount (cell number) normalized to surface area of human fetal osteoblast with respect to an average crystal grain size of 0.5 μm of type 304 stainless steel sample with different magnetization (UT: untreated; DM: demagnetized; 0.1 T, 0.5 T, and 1.1 T) according to some embodiments. FIG. 12B is a response profile obtained by plotting a response amount (cell number) normalized to surface area of human fetal osteoblast with respect to an average crystal grain size of 5 μm of type 304 stainless steel sample with different magnetization (UT: untreated; DM: demagnetized; 0.1 T, 0.5 T, and 1.1 T) according to some embodiments. FIG. 12C is a response profile obtained by plotting a response amount (cell number) normalized to surface area of human fetal osteoblast with respect to an average crystal grain size of 9 μm of type 304 stainless steel sample with different magnetization (UT: untreated; DM: demagnetized; 0.1 T, 0.5 T, and 1.1 T) according to some embodiments.

DETAILED DESCRIPTION

Figure 1A:
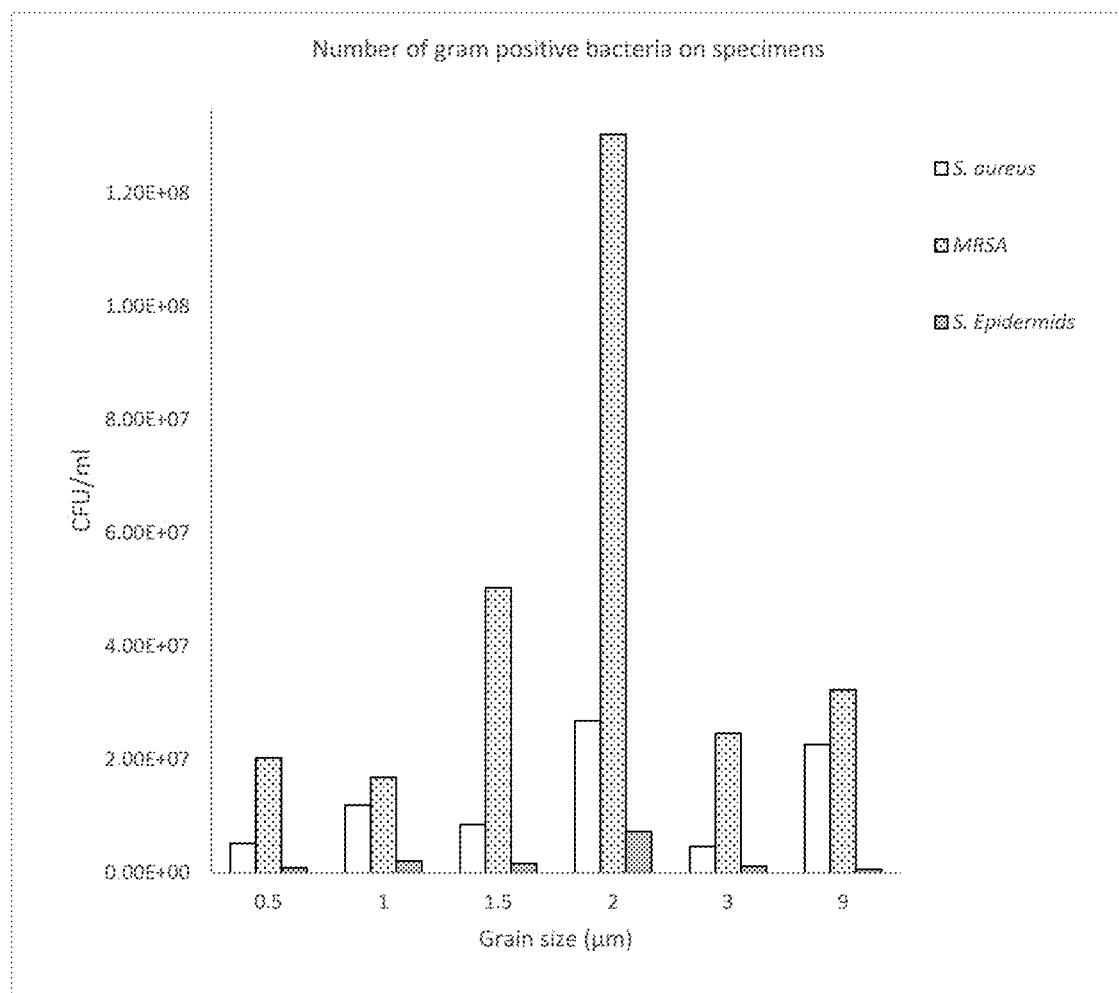
FIG. 1A is an example of a response profile obtained by plotting a response amount (CFU/ml) of gram-positive bacteria (*S. aureus*, Methicillin-resistant *Staphylococcus aureus*, *S. epidermidis*) with respect to an average crystal grain size of a crystal grain according to some embodiments.

Metal materials having refined crystal grains are superior in characteristics such as strength, toughness, and corrosion resistance as compared with metal materials having coarse crystal grains. Accordingly, the metal materials are widely used in various industrial applications such as steel plates and medical devices.

Some aspects of the disclosure relate to a metal that is processed so as to form a recrystallized metal material having an average crystal grain size ranging from 0.01 to 3 μm, 0.02 to 3 μm, 0.05 to 3 μm, 0.1 μm to 3 μm, from 0.2 to 3 μm, from 0.5 μm to 3 μm, from 1 μm to 3 μm, from 2 μm to 3 μm, 0.01 to 2 μm, 0.02 to 2 μm, 0.05 to 2 μm, 0.1 μm to 2 μm, from 0.2 to 2 μm, from 0.5 μm to 2 μm, from 1 μm to 2 μm, 0.01 to 1 μm, 0.02 to 1 μm, 0.05 to 1 μm, 0.1 μm to 1 μm, from 0.2 to 1 μm, from 0.5 μm to 1 μm, 0.01 to 0.6 μm, 0.02 to 0.6 μm, 0.05 to 0.6 μm, 0.1 μm to 0.6 μm, from 0.2 to 0.6 μm, from 0.5 μm to 0.6 μm, 0.01 to 0.5 μm, 0.02 to 0.5 μm, 0.05 to 0.5 μm, 0.1 μm to 0.5 μm, from 0.2 to 0.5 μm, about 0.01 μm, about 0.02 μm, about 0.03 μm, about 0.04 μm, about 0.05 μm, about 0.06 μm, about 0.07 μm, about 0.08 μm, about 0.09 μm, about 0.1 μm, about 0.2 μm, about 0.3 μm, about 0.4 μm, about 0.5 μm, about 0.6 μm, about 0.7 μm, about 0.8 μm, about 0.9 μm, about 1 μm, about 2 μm, about 3 μm or higher or any range therebetween. In some embodiments, the metal is processed so as to form a recrystallized metal material having an average crystal grain size ranging from 0.2 μm to 0.5 μm.

It should be appreciated that the metal material can have a homogenous average crystal grain size. In some embodiments, the metal comprises an average grain size of about 0.1 μm±20%, about 0.2 μm±20%, about 0.3 μm±20%, about 0.4 μm±20%, about 0.5 μm±20%, about 0.6 μm±20%, about 0.7 μm±20%, about 0.8 μm±20%, about 0.9 μm±20%, about 1 μm±20%, about 2 μm±20%, about 3 μm±20% or any range therebetween. In some embodiments, the metal comprises an average grain size of about 0.1 μm±40%, about 0.2 μm±40%, about 0.3 μm±40%, about 0.4 μm±40%, about 0.5 μm±40%, about 0.6 μm±40%, about 0.7 μm±40%, about 0.8 μm±40%, about 0.9 μm±40%, about 1 μm±40%, about 2 μm±40%, about 3 μm±40%, or any range therebetween.

In some aspects, the metal is type 304 stainless steel metal having an average crystal grain size ranging from about 0.10 µm to about 3 µm, for example 0.2 to 0.5 µm. In some embodiments, the type 304 stainless steel metal has a composition described at Table 4.

In some aspects, the metal is type 316 stainless steel metal having an average crystal grain size ranging from about 0.1 µm to about 3 µm, for example, 0.2 µm to 0.5 µm. In some embodiments, the type 316 stainless steel metal has a composition described at Table 5.

In some aspects, the metal is titanium or titanium alloy having a crystal grain size ranging from about 0.8 µm to about 9 µm, for example 0.8 to 8.80 µm. In some embodiments, the titanium alloy is β-titanium (Ti-15V-3Cr-3Sn-3Al), Ti-6Al-4V, or combinations thereof.

In some embodiments, the metal material can be processed to tailor the crystal grain size so as to control cell adhesion, cell growth or combination thereof. In some embodiments, the metal material or device can have an average grain size to inhibit adhesion, growth or combination thereof of bacteria. In some embodiments, the metal material or device can have an average grain size to increase the adhesion, growth or combinations thereof of predetermined eukaryotic cells. In some embodiments, the metal material or device can have an average grain size to inhibit adhesion, growth or combination thereof of predetermined eukaryotic cells. In some embodiments, the metal material or device can have (i) an average grain size to inhibit adhesion, growth or combination thereof of bacteria, (ii) an average grain size to promote adhesion, growth or combination thereof of predetermined eukaryotic cells and (iii) an average grain size to inhibit adhesion, growth or combination thereof of predetermined eukaryotic cells.

Metal Material Having Antibiotic Property

The term "antibiotic property" as used herein refer to property of preventing or reducing the growth or reproduction or adhesion of a microorganism (such as bacterial and fungal organisms), or of killing a microorganism.

The term "bacterial and fungal organisms" as used in the present invention means all genus and species of bacteria and fungi, including but not limited to all spherical, rod-shaped, and spiral bacteria. Non-limiting examples of bacteria include staphylococci (e.g., *Staphylococcus epidermidis*, *Staphylococcus aureus*), *Enterrococcus faecalis*, *Pseudomonas aeruginosa*, *Escherichia coli*, *Clostridioides difficile* among other gram-positive bacteria and gram-negative bacilli. Non-limiting examples of fungal organisms include *Candida albicans, Candida krusei, Candida parapsilosis, Candida* spp, *Candida pseudotropicalis, Candida glabrata, Candida lusitaniae,* and *Candida tropicalis.*

In some embodiments, the bacteria are gram-positive bacteria including, but not limited to, *Staphylococcus aureus, Staphylococcus epidermidis,* Methicillin-resistant *Staphylococcus aureus* (MRSA), or the like. In some embodiments, the bacteria are gram-negative bacteria including, but not limited to, *Pseudomonas aeruginosa, E. coli, Klebsiella pneumoniae, Legionella pneumophila, Proteus mirabilis, Enterobacter cloacae, Serratia marcescens, Helicobacter pylori, Salmonella enteritidis,* and *Salmonella typhi.*

Aspects of the invention provide for a metal material and methods for providing efficacious broad spectrum anti-infective protection to a metal material, including but not limited to, protection against resistant staphylococci, MDR gram-negative bacteria (such as MDR *Pseudomonas aeruginosa*).

Aspects of the invention provide metal material having an improved antibiotic property. In some embodiments, the metal material can be used in medical devices, such as implants (for example, but not limited to orthopedic implants). In some embodiments, the metal material can be used in surgical instruments, vascular stent, endoscopic instruments, catheter parts, guide wire, kirschner wires (K-wire), plates, pins, screw, needles, pacemaker leads, dental brace, etc. or implantable medical devices. In some embodiments, the metal material can be used in surgical instruments. In some embodiments, the metal material can be used in biosensors. In some embodiments, the metal material can be used in kitchenware. In some embodiments, the metal material can be used in experimental tools. In some embodiments, the metal material can be used in a kirschner wire.

Non-limiting examples of medical devices include vascular catheters, such as peripherally insertable central venous catheters, dialysis catheters, long term tunneled central venous catheters, peripheral venous catheters, single-lumen and multiple-lumen short-term central venous catheters, arterial catheters, pulmonary artery Swan-Ganz catheters, and the like, urinary catheters, other long term urinary devices, tissue bonding urinary devices, renal stents, penile prostheses, vascular grafts, vascular access ports, wound drain tubes, hydrocephalus shunts, ventricular drainage catheters, neurologic and epidural catheters, neurostimulators, peritoneal dialysis catheters, pacemaker capsules, artificial urinary sphincters, small or temporary joint replacements, dilators, heart valves, orthopedic prosthesis, spinal hardware, surgical site repair mesh (e.g., hernia mesh), endotracheal tubes, biliary stents, gastrointestinal tubes, colorectal tract implants, male and female reproductive implants, cosmetic or reconstructive implants, stethoscope drums, orthopedic implants (e.g., joint (knee, hip, elbow, shoulder, ankle), prostheses, external fixation pins, intramedullary rods and nails, spine implants), cardiac pacemakers, defibrillators, electronic device leads, adaptors, lead extensions, implantable infusion devices, implantable pulse generators, implantable physiological monitoring devices, devices for locating an implantable pulse generator or implantable infusion device under the skin, and devices (e.g. refill needles and port access cannulae) for refilling an implantable infusion device or other medical and indwelling devices that may be subject to microbial infestation.

In some embodiments, the device are stainless steel devices and can be used for, but not limited to, high speed surgical drill, vertebroplasty and kyphoplasty devices, minimally invasive surgical instruments and endoscopy devices, orthopedic implants, and surgical instruments.

In some embodiments, the device are titanium devices and can be used for but not limited to, orthopedic implants, dental implants, spinal implants, minimally invasive surgical instruments and endoscopy devices, and surgical instruments.

In some embodiments, the antibiotic property of the metal material is achieved without the addition of an antibiotic agent in or onto the metal material.

In some embodiment, the metal material inhibits adhesion of bacterial cells by 100%, 95%, 90%, 80%, 70%, 60%, 50%, 40%, 30%, 20%, 10%, or by at least by 5% or any value or range therebetween.

Metal Material Promoting Cell Adhesion or Inhibiting Cell Adhesion

In some embodiments, it is desirable to increase the adhesion of cells onto a metallic material, such as metallic implant. In other embodiments, it is desirable the decrease or inhibit the adhesion of cells onto a metallic material, such as a metallic implant. For example, it may be desirable to increase the adhesion of osteoblast on the surface of the orthopedic implant. In other examples it may be desirable to increase the adhesion of endothelial cells on the surface of the vascular stents or implant and to inhibit the adhesion of fibroblast onto the vascular stents or implant.

In some embodiments, the metal material described herein can improve the adhesion and/or growth of eukaryotic cells such as osteoblasts, fibroblasts, chondrocytes, endothelial cells, keratinocytes, smooth muscle cells, urothelial cells, osteoclasts, osteocytes, stem cells, mesenchymal stem cells, induced pluripotent stem cells, neurons, astrocytes, Schwann cells, meningeal cells, epithelial cells, etc. . . . .

In some embodiments, the metal material described herein has a surface energy that promotes cell adhesion and/or growth of some eukaryotic cells. In some embodiment, the metal material increases cell adhesion and/or growth by at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or any value or range therebetween.

Yet in some embodiments, the metal material described herein has a surface energy that inhibits cell adhesion and/or growth of other eukaryotic cells. In some embodiment, the metal material decreases cell adhesion and/or growth at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or any value or range therebetween.

In some embodiments, the metal material described herein has antibiotic properties and improve the adhesion and/or growth of eukaryotic cells such as osteoblasts, fibroblasts, endothelial cells, chondrocytes, endothelial cells, keratinocytes, smooth muscle cells, urothelial cells, osteoclasts, osteocytes, stem cells, mesenchymal stem cells, induced pluripotent stem cells, neurons, astrocytes, Schwann cells, meningeal cells, epithelial cells, etc. . . . .

In some embodiments, the metal material described herein has antibiotic properties and inhibits the adhesion and/or growth of eukaryotic cells such as immune cells.

The metal material and the use of the metal material to (i) reduce or inhibit bacterial adhesion and/or growth, (ii) improve or to the adhesion and/or growth of eukaryotic cells such as osteoblasts, fibroblasts, etc, (iii) reduce or inhibit adhesion and/or growth of immune cells, or (iv) (i) reduce or inhibit bacterial adhesion and/or growth, (ii) improve adhesion and/or growth of eukaryotic cells such as osteoblasts, fibroblasts etc, (iii) reduce or inhibit adhesion and/or growth of immune cells or any combinations of (i), (ii) and (iii) is described herein below.

Uses of Metal Material

In some embodiments, the metal material can be used in medical devices. For example, the metal material can be used in vascular stent, endoscopic instruments, surgical instruments, catheter parts, guide wire, kirschner wires, pins, plates, screw, etc., or implantable medical devices.

In some embodiments, the metal material can be used in biosensors. In some embodiments, the metal material can be used in kitchenware. In some embodiments, the metal material can be used in experimental tools.

Non-limiting examples of medical devices include vascular catheters, such as peripherally insertable central venous catheters, dialysis catheters, long term tunneled central venous catheters, peripheral venous catheters, single-lumen and multiple-lumen short-term central venous catheters, arterial catheters, pulmonary artery Swan-Ganz catheters, and the like, urinary catheters, other long term urinary devices, tissue bonding urinary devices, renal stents, penile prostheses, vascular grafts, vascular access ports, wound drain tubes, hydrocephalus shunts, ventricular drainage catheters, neurologic and epidural catheters, neurostimulators, peritoneal dialysis catheters, pacemaker capsules, artificial urinary sphincters, small or temporary joint replacements, dilators, heart valves, orthopedic prosthesis, spinal hardware, surgical site repair mesh (e.g., hernia mesh), endotracheal tubes, biliary stents, gastrointestinal tubes, colorectal tract implants, male and female reproductive implants, cosmetic or reconstructive implants, stethoscope drums, orthopedic implants (e.g., joint (knee, hip, elbow, shoulder, ankle), prostheses, external fixation pins, intramedullary rods and nails, spine implants), cardiac pacemakers, defibrillators, electronic device leads, adaptors, lead extensions, implantable infusion devices, implantable pulse generators, implantable physiological monitoring devices, devices for locating an implantable pulse generator or implantable infusion device under the skin, and devices (e.g. refill needles and port access cannulae) for refilling an implantable infusion device or other medical and indwelling devices that may be subject to microbial infestation.

Some embodiments relate to surgical instruments.

In some embodiments, the device is a K-wire.

In some embodiments, the device is an implantable orthopedic implant.

In some embodiments, the device is a vascular stent.

Composition

Known metal materials for medical device application may be used, and examples of the metal materials include iron, stainless steel, aluminum, silver, copper, titanium, tin, nickel, zinc, chromium, and alloys of these metal materials. Among them, stainless steel is preferable in view of easy controllability of the crystal grain size of the crystal grain, versatility, ready availability, processability, and low toxicity. The stainless steel is not particularly limited, and may be any of martensitic stainless steel, ferritic stainless steel, austenitic stainless steel, austenite/ferrite stainless steel, and precipitation hardening stainless steel.

In some embodiments, the metal material is stainless steel or a stainless-steel alloy. For example, the metal material can be type 304 stainless steel or type 316 stainless steel. The type 316 stainless steel differs from the type 304 by the presence of molybdenum. In some embodiments, the stainless steel material can comprise from 6 to 22% nickel. In some embodiments, the stainless steel material can also contain other alloying elements, such as chromium (16 to 26%) for corrosion resistance. In some embodiments, the stainless steel can comprise manganese and molybdenum. In some embodiments, the type 316 stainless steel can be used for medical devices.

In some embodiments, the metal material is titanium or titanium alloy. In some embodiments, the metal material is cobalt chromium. In some embodiments, the metal material is cobalt chromium molybdenum. In some embodiments, the metal material is nitinol.

Nanostructure

According to aspects of the invention, the metal material provided herein has a nanostructure not limited to the surface. For example, the metal material can keep its nanostructure throughout its processing resulting in a metal material having a homogeneous nanostructure.

The metal material according to some embodiments is made of a fine crystal grain, which allows for the application to a wide range of devices. The metal material has a homogeneous nanostructure. The predetermined average crystal grain size nanostructure (for example from 0.2 μm to 0.5 μm) is consistent throughout the material, i.e. on the surface and within the material.

The crystal grain forming the metal material according to some embodiments has an average crystal grain size for controlling the biological property of the metal material.

Aspects of the invention is based the phenomenon that biological property of the metal material depends on the average crystal grain size of the metal material.

In some aspects of the invention, the metal material described herein can have a crystal grain size, surface free energy and roughness that (i) reduces or inhibits bacterial adhesion and/or growth, (ii) improves or increases the adhesion and/or growth of eukaryotic cells such as osteoblasts, fibroblasts, etc, (iii) reduces or inhibits adhesion and/or growth of immune cells, or (iv) (i) reduce or inhibit bacterial adhesion and/or growth, (ii) improve adhesion and/or growth of eukaryotic cells such as osteoblasts, fibroblasts etc, (iii) reduce or inhibit adhesion and/or growth of immune cells or any combinations of (i), (ii) and (iii).

In some aspects of the invention, the metal material described herein can have a crystal grain size that is about the size of eukaryotic cells of a tissue under consideration and promote the adhesion and/or growth of the cells to the metal. In addition, the metal material described herein can have a surface free energy that promote the adhesion and/or growth of the cells to the metal. Furthermore, the metal material described herein can have a roughness that promote the adhesion and/or growth of the cells to the metal.

In some aspects of the invention, the metal material described herein can have a crystal grain size inhibits the adhesion and/or growth of the cells to the metal. In addition, the metal material described herein can have a surface free energy that promote the adhesion and/or growth of the cells to the metal. Furthermore, the metal material described herein can have a roughness that inhibits the adhesion and/or growth of the cells to the metal. In some embodiments, the cells are prokaryotic cells and/or eukaryotic cells.

Some aspects of the invention are based the phenomenon that antibiotic property of the metal material depends on the average crystal grain size of the metal material. In some embodiments, the metal material having a predetermined average crystal grain size ranging from about 0.1 to 3 μm. In some embodiments, the metal material having a predetermined average crystal grain size ranging from 0.2 to 1 μm. In some embodiments, the metal material having a predetermined average crystal grain size ranging from 0.2 to 0.5 μm. In some embodiments, the metal material provided herein can the growth of microorganisms and/or improve growth of osteoblasts and fibroblast. In some embodiments, the metal material provided herein can inhibit the growth, the immobilization or the growth and the immobilization (adsorption) of the microorganisms. In some embodiments, the metal material provided herein can inhibit the growth, the immobilization or the growth and the immobilization (adsorption) of the immune cells. In some embodiments, the metal material provided herein promotes the growth, the immobilization or the growth and the immobilization (adsorption) of predetermined eukaryotic cells.

Aspects of the invention relate to methods for inhibiting the growth, immobilization or growth and immobilization of microorganisms.

In some embodiments, the average crystal grain size for inhibiting the growth and/or immobilization of microorganisms can range from 0.01 to 3 μm, 0.02 to 3 μm, 0.05 to 3 μm, 0.1 μm to 3 μm, from 0.2 to 3 μm, from 0.5 μm to 3 μm, from 1 μm to 3 μm, from 2 μm to 3 μm, 0.01 to 2 μm, 0.02 to 2 μm, 0.05 to 2 μm, 0.1 μm to 2 μm, from 0.2 to 2 μm, from 0.5 μm to 2 μm, from 1 μm to 2 μm, 0.01 to 1 μm, 0.02 to 1 μm, 0.05 to 1 μm, 0.1 μm to 1 μm, from 0.2 to 1 μm, from 0.5 μm to 1 μm, 0.01 to 0.6 μm, 0.02 to 0.6 μm, 0.05 to 0.6 μm, 0.1 μm to 0.6 μm, from 0.2 to 0.6 μm, from 0.5 μm to 0.6 μm, 0.01 to 0.5 μm, 0.02 to 0.5 μm, 0.05 to 0.5 μm, 0.1 μm to 0.5 μm, from 0.2 to 0.5 μm, about 0.01 μm, about 0.02 μm, about 0.03 μm, about 0.04 μm, about 0.05 μm, about 0.06 μm, about 0.07 μm, about 0.08 μm, about 0.09 μm, about 0.1 μm, about 0.2 μm, about 0.3 μm, about 0.4 μm, about 0.5 μm, about 0.6 μm, about 0.7 μm, about 0.8 μm, about 0.9 μm, about 1 μm, about 2 μm, about 3 μm or higher or any range therebetween. In some embodiments, the average crystal grain size for inhibiting the growth and/or immobilization of microorganisms can range from 0.2 μm to 0.5 μm.

In some embodiments, the average crystal grain size is greater than 0.1 μm but smaller than 3 μm. In some embodiments, the average crystal grain size is greater than 0.2 μm but smaller than 1 μm. In some embodiments, the average crystal grain size is greater than 0.2 μm but smaller than 0.7 μm. In some embodiments, the average crystal grain size is greater than 0.2 μm but smaller than 0.5 μm. In some embodiments, the average crystal grain size is greater than 0.2 μm but smaller than 0.4 μm. In some embodiments, the average crystal grain size is greater than 0.2 μm but smaller than 0.3 μm. In some embodiments, the average crystal grain size is greater than 0.3 μm but smaller than 0.5 μm. In some embodiments, the average crystal grain size is greater than 0.4 μm but smaller than 0.5 μm.

The grain boundaries can be measured by Electron backscatter diffraction (EBSD) and can show the different atoms low angles. The difference of angle can be greater 5 degrees. Each grain can be determined by an area surrounded by the grain-boundary lines. When the grain size is large, the shape is unique and random polygon. As the grain become smaller, the shape become smaller polygon, similar to a circle, a cubic, or rectangle. The short length for rectangle or diameter for circle is about the average grain size.

In some embodiments, the metal material has an average grain size of about 0.5 μm (+/−20%) or between 0.2 μm and 0.5 μm and inhibits the growth of gram-positive and gram-negative bacteria.

During refining the crystal grain, the chemical composition of metal material does not change. Thus, any metal of different chemical composition can be used as long as it is a metal material having crystals or grains, such as for titanium, titanium-based materials, stainless steel, Co—Cr alloys, Co—Cr—Mo, nitinol, platinum, palladium, etc.

In some embodiments, the metal material, in addition to its antibiotic property has an improved tensile strength and hardness than conventional stainless steel.

As the method of adjusting the average crystal grain size of the crystal grain, a refinement method can be adopted. Examples of the method include a rolling process for the metal raw material before refinement, a shearing process, a compression process, a deforming process, and a combination of the processes. In this case, cooling or heating may be carried out, or refinement may be carried out in an atmosphere in the presence or absence of a specific gas (such as oxygen or nitrogen). Generally, the refinement is progressed by heating leading to plastic deformation and recrystallization by cooling. The above procedure is carried out once or repeated multiple times, thereby obtaining a desired average crystal grain size.

According to aspects of the invention, the device formed from the metal material provided herein has a nanostructure not limited to the surface. For example, the metal material can keep its nanostructure throughout its processing resulting in a metal material having a homogeneous nanostructure.

According to some embodiments, the magnetic fields of the metal material provided herein can alter surface charges as well as initial protein adsorption events to in turn change bacteria attachment and colonization and/or growth of eukaryotic cells.

Polished/Unpolished Metal Material

In some embodiments, the metal material can be polished to change the surface roughness. In some embodiments, the method of polishing the metal material comprises rough polishing using lapping film (see Example 4).

The surface roughness can be calculated with an atomic force microscope (AFM) and three different parameters can be obtained for the metal material—the root mean square roughness (Rq), the arithmetic roughness (Ra) and the maximum height (Rz).

TABLE 1

| Polish Samples | Rq (nm) | Ra (nm) | Rz (nm) |
| --- | --- | --- | --- |
| 304-0.5 | 2.218 | 1.605 | 24.180 |
| 304-1.5 | 2.729 | 2.006 | 119.350 |
| 304-9 | 2.391 | 1.750 | 4.490 |
| 316-1.5 | 2.376 | 1.809 | 52.760 |
| 316-10 | 2.606 | 2.044 | 77.020 |

TABLE 2

| Non-polish Samples | Rq (nm) | Ra (nm) | Rz (nm) |
| --- | --- | --- | --- |
| 304-0.5 | 5.978 | 4.654 | 54.790 |
| 304-1 | 8.725 | 6.962 | 60.926 |
| 304-1.5 | 6.183 | 4.864 | 49.116 |
| 304-2 | 7.138 | 5.706 | 49.938 |
| 304-3 | 6.633 | 4.872 | 76.560 |
| 304-9 | 3.630 | 2.868 | 29.778 |
| 316-1.5 | 9.923 | 7.797 | 77.923 |
| 316-10 | 8.660 | 6.587 | 72.594 |

In some embodiments, the material is polished has a surface roughness at the nanoscale from about 0.1 nm to 100 µm.

Previous studies showed that the optimal value of surface energy to inhibit bacteria growth is around 42 m N/m, (See Liu et al., "Understanding the Role of Polymer Surface Nanoscale Topography on Inhibiting Bacteria Adhesion and Growth" Biomaterials Science and Engineering, 2016, 2 (1), pp 122-130.)

In some embodiments, the value of surface energy of the metal material is between 40 to 45 mN/m, 40-47 mN/m, 40 and 50 mN/m, 40 to 55 mN/m, 40 to 60 mN/m, 35 to 45 mN/m, 35 to 50 mN/m, 35 to 55 mN/m, 35 to 60 mN/m, 30 to 45 mN/m, 30 to 50 mN/m, 30 to 55 mN/m, 30 to 60 mN/m.

In some embodiments, the metal material described herein has a surface energy that promotes growth of some eukaryotic cells. Yet in some embodiments, the metal material described herein has a surface energy that inhibits growth of other eukaryotic cells. For example, the surface energy can promote the attachment and the growth of endothelial cells and inhibit the attachment and/or growth of fibroblast.

In some embodiments, the value of surface energy of the metal material to promote growth of eukaryotic cells is between 40 to 45 mN/m, 40-47 mN/m, 40 and 50 mN/m, 40 to 55 mN/m, 40 to 60 mN/m, 35 to 45 mN/m, 35 to 50 mN/m, 35 to 55 mN/m, 35 to 60 mN/m, 30 to 45 mN/m, 30 to 50 mN/m, 30 to 55 mN/m, 30 to 60 mN/m.

Optimal Ra, Rq, Rz can be calculated with the Khang's equation using 45 mN/m for the ideal surface energy.

$$Es = E0 + \rho \times reff$$

ES=surface energy
Eo,s=ground Surface energy
reff=roughness
ρ=coupling constant

In some embodiments, the metal material can have a surface energy tailored to the adsorption of proteins that decrease inflammatory cell functions, decrease bacterial functions, increase bone cell functions, increase endothelial cell functions or any combinations of the foregoing.

In some embodiments, the metal material can have an average grain size tailored to the adsorption of proteins that decrease inflammatory cell functions, decrease bacterial functions, increase bone cell functions, increase endothelial cell functions or any combinations of the foregoing.

Without being bound to the theory, changes in surface energy in turn can change initial protein adsorption to, for example, inhibit bacteria attachment and colonization.

In some embodiments, the metal material can be polished or unpolished. In some embodiments, the polished and/or unpolished metal material has an average grain size is between about 100 nm and 10 µm, for example less than 500 nm, for example about 100 nm, for decreasing attachment or growth of both gram-positive and gram-negative bacteria. In some embodiments, the polished and/or unpolished metal material has an average grain size is preferably between about 1 and 3 µm.

Shape/Devices

The shape of the metal material according to some embodiments is not particularly limited, and any shape such as a plate shape, a line shape, a rod shape, a spherical shape or a cylindrical shape can be adopted. In some embodiments, the metal material is in the shape of a wire or line.

In some embodiments, the metal material is in the form of a plate or foil with a thickness ranging from about 0.1 mm to 1 mm, from example 0.1 mm, 0.2 mm, 0.3 mm, 0.4 mm, 0.5 mm, 0.5 mm, 0.6 mm, 0.7 mm, 0.8 mm, 0.9 mm, or 1 mm.

In some embodiments, the metal material is in the form of a bar or wire with a dimeter of from 0.02 mm to 6 mm.

Method of Inhibiting Growth of Microorganism

The method of inhibiting growth of microorganism according to some embodiments is a method using the metal material including the predetermined average crystal grain.

In some embodiments, a metal material, for example, a stainless steel material, is provided in which each average crystal grain size of crystal grains is adjusted within a range of from 0.01 to 3 µm, 0.02 to 3 µm, 0.05 to 3 µm, 0.1 µm to 3 µm, from 0.2 to 3 µm, from 0.5 µm to 3 µm, from 1 µm to 3 µm, from 2 µm to 3 µm, 0.01 to 2 µm, 0.02 to 2 µm, 0.05 to 2 µm, 0.1 µm to 2 µm, from 0.2 to 2 µm, from 0.5 µm to 2 µm, from 1 µm to 2 µm, 0.01 to 1 µm, 0.02 to 1 µm, 0.05 to 1 µm, 0.1 µm to 1 µm, from 0.2 to 1 µm, from 0.5 µm to 1 µm, 0.01 to 0.6 µm, 0.02 to 0.6 µm, 0.05 to 0.6 µm, 0.1 µm to 0.6 µm, from 0.2 to 0.6 µm, from 0.5 µm to 0.6 µm, 0.01 to 0.5 µm, 0.02 to 0.5 µm, 0.05 to 0.5 µm, 0.1 µm to 0.5 µm, from 0.2 to 0.5 µm, about 0.01 µm, about 0.02 µm, about 0.03 µm, about 0.04 µm, about 0.05 µm, about 0.06 µm, about 0.07 µm, about 0.08 µm, about 0.09 µm, about 0.1 µm, about 0.2 µm, about 0.3 µm, about 0.4 µm, about 0.5 µm, about 0.6 µm, about 0.7 µm, about 0.8 µm, about 0.9 µm, about 1 µm, about 2 µm, about 3 µm or higher or any range therebetween. In some embodiments, the average crystal grain size can range from 0.2 µm to 0.5 µm. In some embodiments, the average crystal grain size is greater than 0.2 µm but smaller than 1 µm. In some embodiments, the average crystal grain size is greater than 0.1 µm but smaller than 3 µm. In some embodiments, the average crystal grain size is greater than 0.2 µm but smaller than 0.5 µm.

In some embodiments, the average crystal grain size of the crystal grain for giving the optimal inhibition for microorganism growth is determined based on the response profile obtained in the above procedure.

Figure 1B:
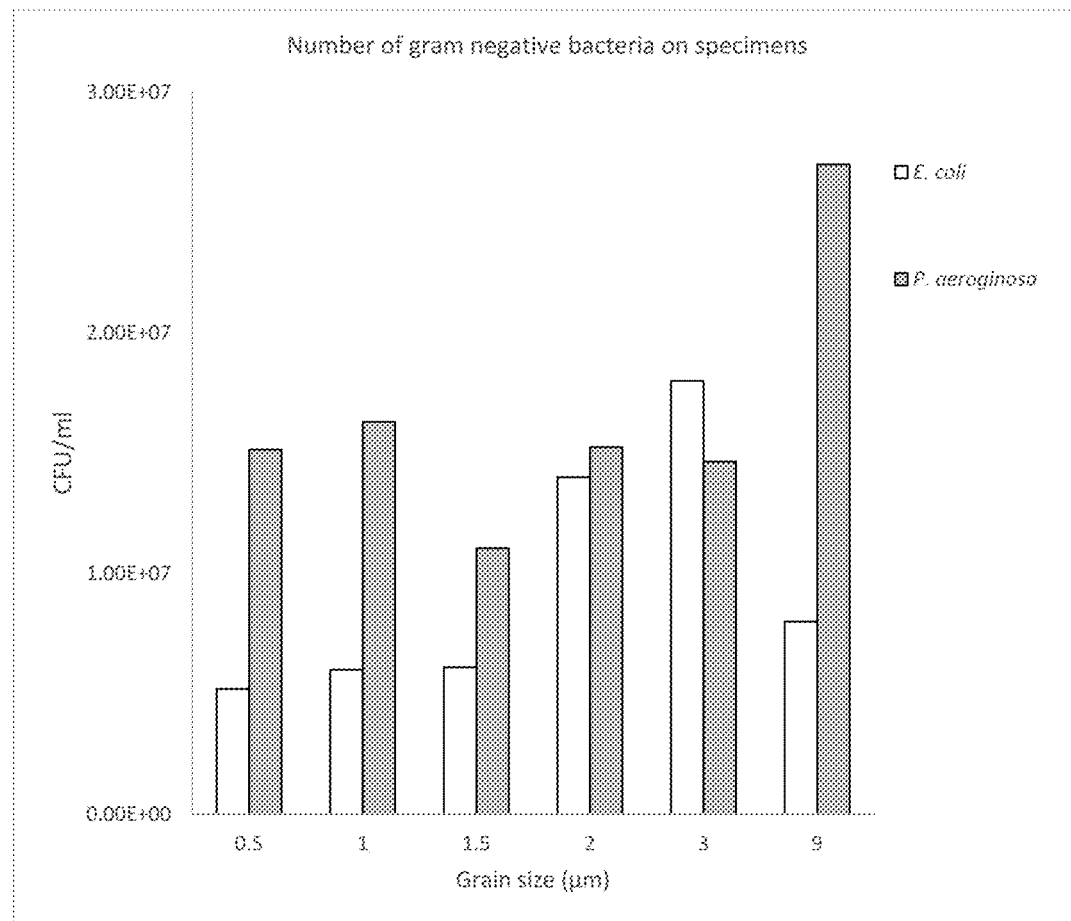
FIG. 1B is an example of a response profile obtained by plotting a response amount (CFU/ml) of gram-negative bacteria (*E. coli*, *P. aeruginosa*) with respect to an average crystal grain size of a crystal grain according to some embodiments.

FIG. 1A shows antibiotic properties of the metal material on gram-positive bacteria. For example, FIG. 1A shows that metal material having a grain size of 0.5 µm, 1 µm, 1.5 µm, 3 µm and 9 µm inhibits growth/adhesion of gram-positive bacteria. FIG. 1B shows antibiotic properties of the metal material on gram-negative bacteria. For example, FIG. 1B shows that metal material having a grain size of 0.5, 3 and 9 µm inhibits growth/adhesion of gram-positive bacteria.

Methods of Using to Promoting or Inhibit Cell Adhesion and/or Growth

In some embodiments, the devices can be implanted at the following anatomical locations: subcutaneous, intraperitoneal, intramuscular, intravascular, intraocular, intracerebral or other appropriate sites.

In some embodiments, the nanostructure of the metal material can be tailored to match proteins at the nanometer scale and cells at the micrometer scale. In some embodiments, the crystal grain size can facilitate adhesion of endothelial cells or osteoblast.

In some embodiments, implantable metallic devices are provided having 2 or more surfaces. In some embodiments, the device can comprise a first metal surface configured to have a surface energy that promotes the attachment and/or the growth of a first cell type and a second surface configured to have a surface energy to inhibit the attachment and/or the growth of a second, different cell type. In some embodiments, the device can comprise a first metal surface configured to have an average grain size that promotes the attachment and/or the growth of a first cell type and a second surface configured to have an average grain size to inhibit the attachment and/or the growth of a second, different cell type. For example, the implantable device can be a vascular stent having a first surface configured to promote the attachment and/or the growth of endothelial cells and a second surface configured to inhibit the attachment and/or the growth of fibroblast.

In some embodiments, the metal material can have an average grain size and/or surface energy that inhibit attachment of the cells, growth of the cells or combinations thereof. For example, the metal material can inhibit attachment and/or growth of cells responsible for inflammation, such as immune cells.

Aspects of the disclosure relate to metal material, metal devices or instruments having a homogeneous average crystal grain size nanostructure ranging from 0.2 to 0.5 µm, wherein the metal material, metal devices or instruments inhibit/decrease bacterial growth and biofilm formation. In some embodiments, the metal material, metal devices or instruments can be used for application requiring antibacterial activity. In some embodiments, the application includes surgical instruments, endoscopic devices (e.g. vertebroplasty needle). In some embodiments, the metal is type 304 stainless steel metal. In some embodiments, the metal is type 316 stainless steel metal. In some embodiments, the metal is type 304 stainless steel metal. In some embodiments, the metal is magnetized.

Aspects of the disclosure relate to magnetized metal material, metal devices or instruments having a homogeneous average crystal grain size nanostructure ranging from 0.2 to 0.5 µm, wherein the metal material, metal devices or instruments inhibit/decrease bacterial growth and biofilm formation and promote/increase eukaryotic cell adhesion. In some embodiments, the metal material, metal devices or instruments can be used for application requiring antibacterial action and osseointegration. In some embodiments, the application includes implantable devices and orthopedic implants. In some embodiments, the metal is type 304 stainless steel metal. In some embodiments, the metal is type 316 stainless steel metal. In some embodiments, the metal material has a magnetic moment higher than $2.3 \times 10^7$ emu/$m^3$.

Aspects of the disclosure relate to a stainless steel metal material or article made from stainless steel metal material comprising a homogeneous crystal grain nanostructure and having an average crystal grain size from 0.1 to 3 µm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells. In some embodiments, the stainless steel metal material comprises a homogeneous crystal grain nanostructure and having an average crystal grain size from 0.2 to 1 µm. In some embodiments, the stainless steel metal material comprises a homogeneous crystal grain nanostructure and having an average crystal grain size from 0.2 to 0.5 µm. In some embodiments, the metal material is type 304 stainless steel metal. In some embodiments, the metal material is magnetized. In some embodiments, the metal material is type 316 stainless steel metal. In some embodiments, the metal material is magnetized. In some embodiments, the metal material is magnetized. In some embodiments, the metal material has a magnetic moment higher than $2.3 \times 10^7$ emu/$m^3$.

EXAMPLES

Hereinafter, the present invention will be described in detail with reference to examples, but the present invention is not limited to the following examples unless it exceeds the gist of the present invention.

Example 1: Manufacture of Metal Material

In order to provide metal materials, stainless steel (SUS 304) was subjected to rolling treatment and thermal recrystallization to adjust the average crystal grain sizes of crystal grains to 0.5 µm, 1 µm, 1.5 µm, 2 µm, 3 µm, and 9 µm, respectively. The metal material had a plate shape having a length of 10 mm, a width of 10 mm, and a thickness of 0.1 mm. The rolling treatment and thermal recrystallization were carried out according to the following procedure. Specifically, the stainless steel (SUS 304) was passed through a rotating mill several times and cold-rolled to about 40 to 65% (compression ratio of about 3 to 15% per time). Then, the resulting stainless steel was subjected to annealing at 600 to 850° C. for 10 to 100 seconds (heating rate: 200° C./sec) to recrystallize the stainless steel. Depending on the state of phase transformation, the recrystallized stainless steel was cooled to obtain an austenitic stainless steel (cooling rate: 200 to 400° C./sec.).

It should be appreciated that type 316 stainless steel and other metals can be subjected to the same process to control the average crystal grain size.

The metal material obtained using the rolling treatment and thermal recrystallization described herein has a nanostructure (e.g. average crystal grain size) not limited to the surface. For example, the metal material can keep its nanostructure throughout its processing resulting in a metal material having a homogeneous nanostructure.

Example 2—Measurement of Average Crystal Grain Size

The test sample of the metal material provided above was polished with argon ions using an ion polisher ("IM 4000", manufactured by Hitachi High-Technologies Corporation). Thereafter, the average crystal grain size of the metal material was measured at room temperature in a vacuum environment ($1\times10^{-3}$ Pa) using an electron microscope ("SU-70", manufactured by Hitachi High-Technologies Corporation) having a crystal orientation analysis function. The size of each crystal grain was determined by determining the area of each crystal grain in an arbitrary measurement range (i.e., the observed image; magnification: 1000 times) and calculating a diameter of a circle, assuming that the shape of the crystal grain is a circle having the same area as the area of the crystal grain. The area of the crystal grain and the diameter of the circle having the same area as the area of the crystal grain were calculated using an image processor ("TSL OMI Analysis 7", manufactured by TSL Solutions). Then, the sum of all crystal grain diameters in the arbitrary measurement range was divided by the number of crystal grains, and the resulting value was defined as an average crystal grain size (nm).

Example 3—Antibiotic Properties of Unpolished Metal Material

Methods:

The bacteria were first incubated overnight. After reaching a concentration of $10^5$, the bacteria were mixed with the metal material samples (type 304 stainless steel samples) and incubated for 24 hours. The type 304 stainless steel samples were then washed with distilled water and sonicated for 10 min. After vortexing the samples for an extra 10 seconds, several dilutions of each sample were placed on agar plates. The agar plates were incubated for 12 hours.

Results:

FIG. 1A and FIG. 1B each show an example of the response profile obtained by plotting the colony-forming unit of the gram-positive or gram-negative bacteria after cultivation with respect to the average crystal grain size of the crystal grain.

As shown in FIG. 1A, the number of gram-positive bacteria adsorbed on the metal materials was relatively decreased when the average grain size was 0.5 μm, 1 μm, 1.5 μm, 3 μm and 9 μm showing that the metal materials tested inhibits growth/adhesion of gram-positive bacteria. In particular, FIG. 1A shows a general decrease in the number of gram-positive bacteria on metal material having an average crystal grain size of 0.5 μm. As shown in FIG. 1B the number of bacteria adsorbed on the metal materials was relatively decreased when the average crystal grain size was 0.5 μm, 3 μm and 9 μm showing that the metal materials tested inhibits growth/adhesion of gram-negative bacteria. FIG. 1A shows a general decrease in the number of gram-negative bacteria, in particular *E. coli*, on metal material having an average crystal grain size of 0.5 μm.

Example 4—Antibiotic Properties of Unpolished Metal Material Versus Polished Material Antibiotics properties of unpolished metal material vs polished material were measured.

Methods:

Specimen: Type 304 stainless steel as shown in Table 3: diameter ($\phi$) 11 mm; thickness: 0.1 mm.

TABLE 3

| material | grain size (μm) | C (W %) | Si (W %) | Mn (W %) | P (W %) | S (W %) | Ni (W %) | Cr (W %) |
|---|---|---|---|---|---|---|---|---|
| 304 | 0.5 | 0.05 | 0.39 | 1.10 | 0.030 | 0.004 | 8.03 | 18.01 |
|  | 1.0 |  |  |  |  |  |  |  |
|  | 1.5 |  |  |  |  |  |  |  |
|  | 2.0 |  |  |  |  |  |  |  |
|  | 3.0 |  |  |  |  |  |  |  |
|  | 9.0 |  |  |  |  |  |  |  |

In a first step the specimen was subjected to rough polishing using 3M lapping film whetstone alumina.

The specimen was first polished using a 3M lapping film mesh No. 4000 (3 μm) on the five papers for approximately 40 seconds with hand. The specimen was then polished with a 3M lapping film mesh No. 8000 (1 μm) for approximately 40 seconds with hand. The specimen was then polished with a 3M lapping film mesh No. 15000 (0.3 μm) for approximately 40 seconds with hand.

In a second step the specimen was alumina polished using an alumina solution and buffed using grinding machine on table. The alumina solution used is a mixture solution of φ1 μm alumina and 0.05 μm alumina ($\phi$1 μm alumina: Buehler Micro Polish II Alumina 1.0 μm; $\phi$0.05 μm alumina: BuehlerMasterPrep Polishing Suspension 0.05 μm).

Figure 6:
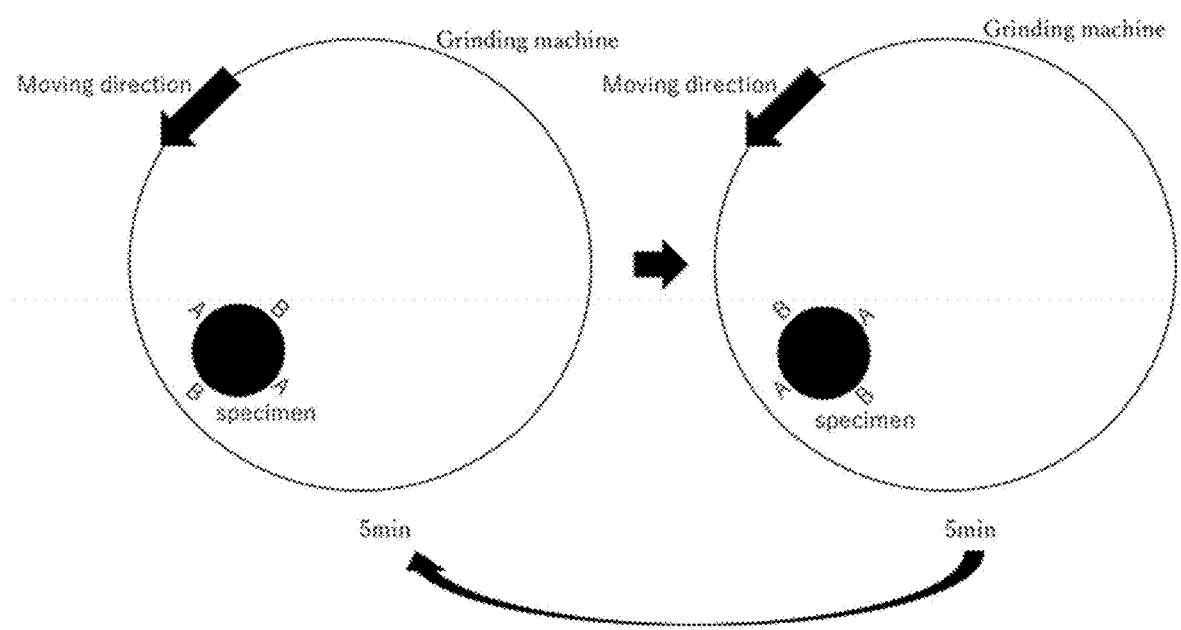
FIG. 6 is a schematic of a polishing method according to some embodiments.

The specimen was polished for five minutes with keeping a first direction A, five minutes with keeping a second direction B five minutes with keeping the direction A and five minutes with keeping the direction B, for a total of 20 minutes polishing as shown on FIG. 6.

In a third step, the specimen was washed with: (1) first with water: first the specimen was washed with hand softly in diluted neutral detergent and tap water, then with running water from bibcock, then the specimen was softly wiped to dry the specimen; (2) then with ethanol by placing the specimen in ethanol and pulling out the specimen and wiping softly to keep specimen to dry the specimen.

Figure 2A:
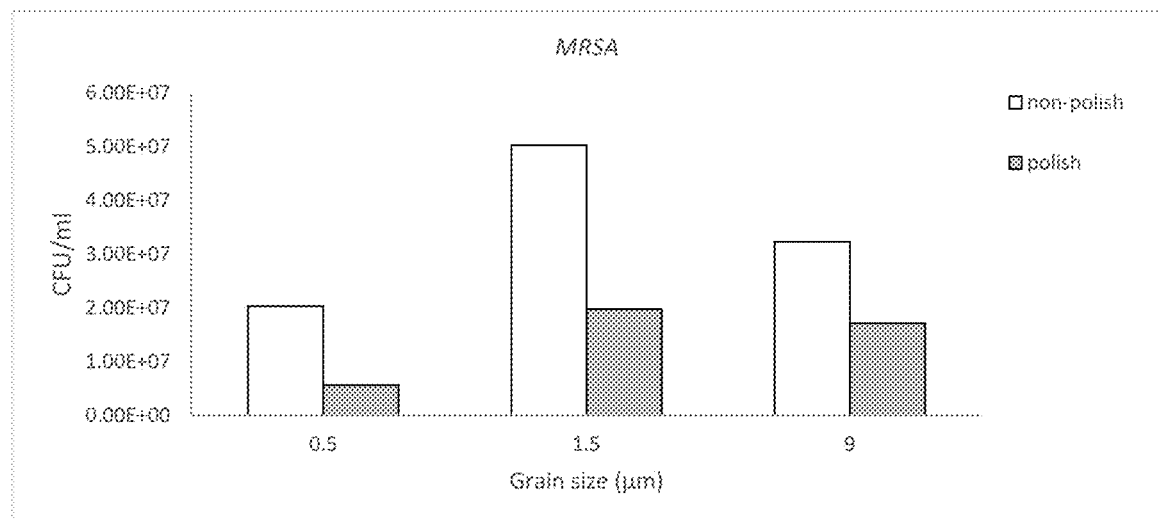
FIG. 2A is an example of a response profile obtained by plotting a response amount (CFU/ml) of gram-positive bacteria MRSA with respect to an average crystal grain size polished or unpolished of a crystal grain according to some embodiments.
Figure 2B:
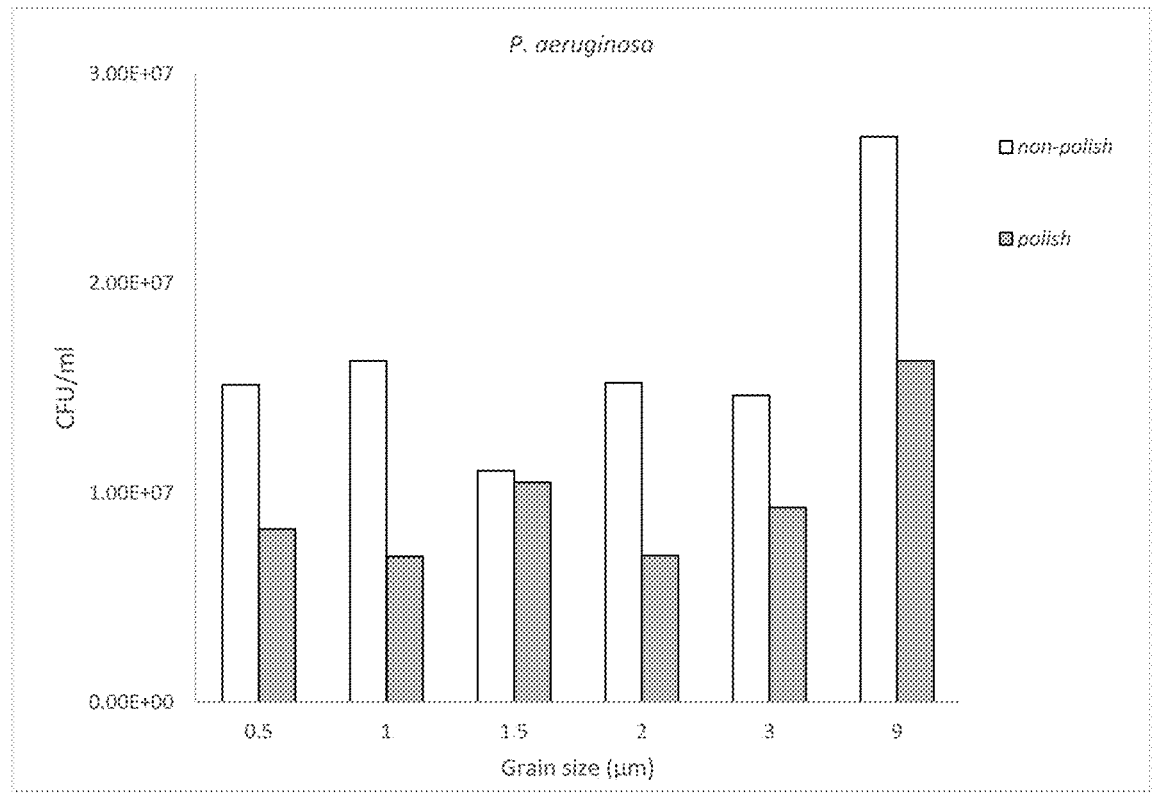
FIG. 2B is an example of a response profile obtained by plotting a response amount (CFU/ml) of gram-negative bacteria *P. aeruginosa* with respect to an average polished or unpolished crystal grain size of a crystal grain according to some embodiments.

FIG. 2A and FIG. 2B show that the number of bacteria adsorbed on the metal materials with an average grain size was 0.5, 1, 1.5. 2, 3 and 9 µm was relatively decreased when the metal material was polished.

Example 5—Cytotoxicity MTS Assay

Methods:
Human fetal osteoblasts (HFOb) were seeded in 12 wells plates with the metal material samples. Cell media was changed every 2 days. For the cell proliferation assay, MTS reagent was added after 3, 5, and 7 days to determine the number of cells alive.

Figure 3A:
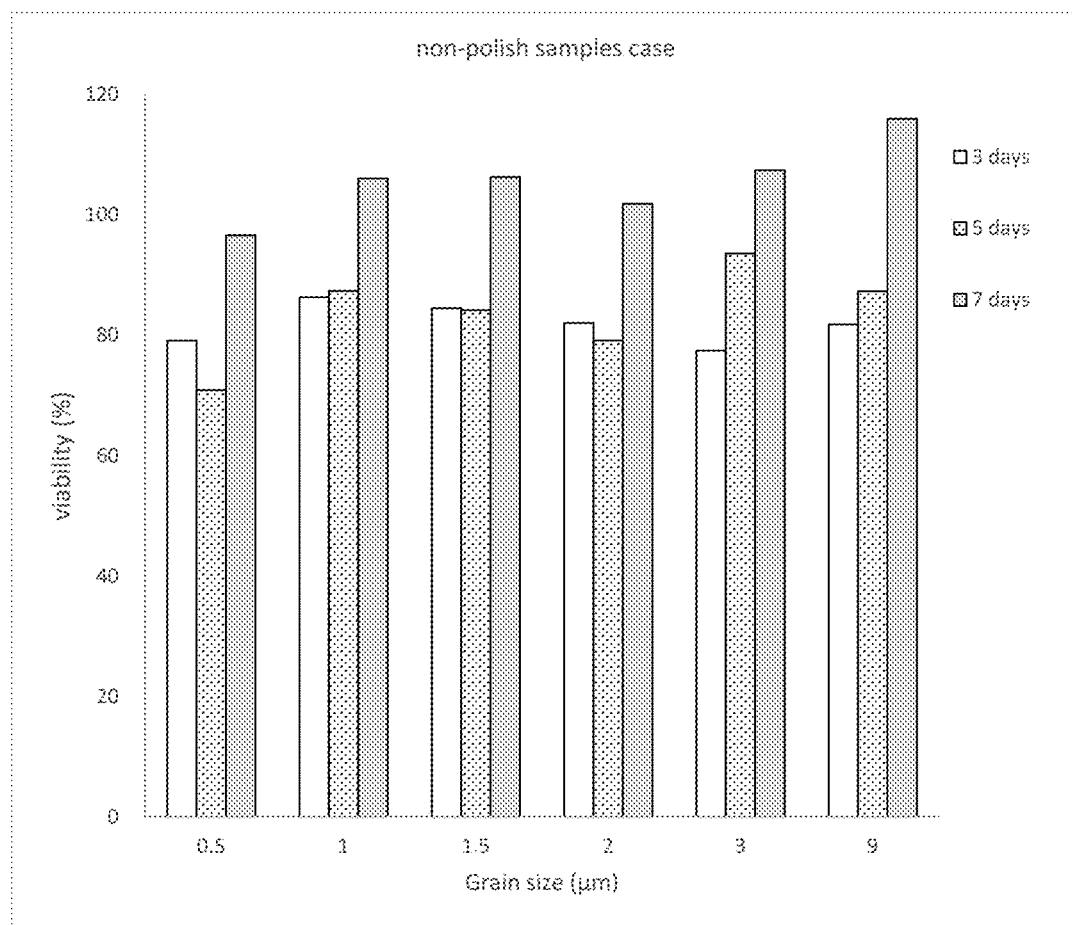
FIG. 3A is an example of a response profile obtained by plotting viability of osteoblast cells with respect to an average unpolished crystal grain size of a crystal grain according to some embodiments.
Figure 3B:
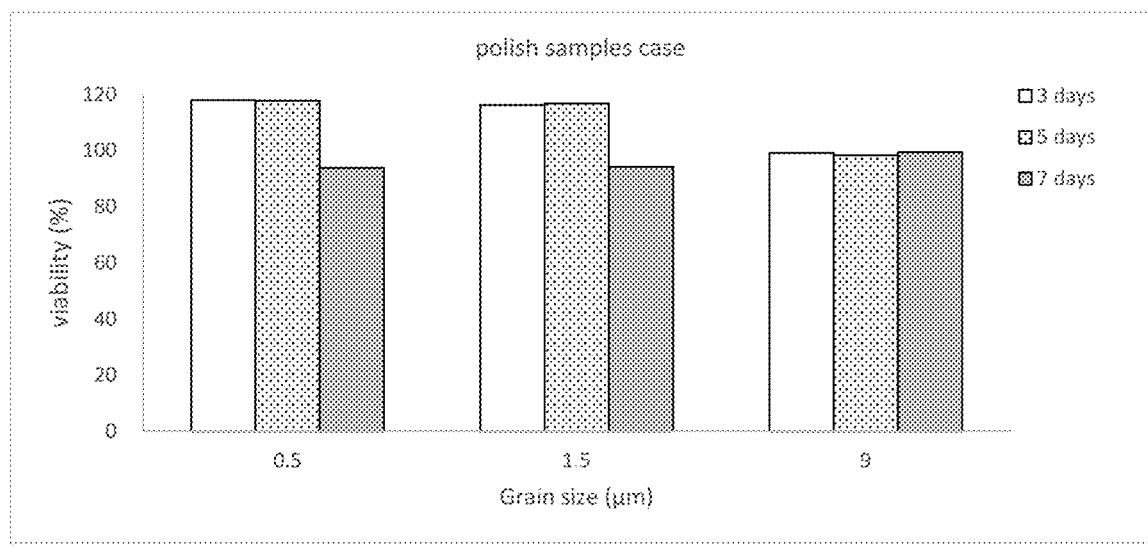
FIG. 3B is an example of a response profile obtained by plotting viability of osteoblast cells with respect to an average polished crystal grain size of a crystal grain according to some embodiments.

Results:
FIG. 3A and FIG. 3B show that the metal material has no cytotoxicity. For most of the samples, the viability was 80% or higher for all three readings (3, 5, and 7 days). For day 7, all readings showed a viability of 100% or higher. Higher viability showed that the metal material samples promoted cell growth.

For polished samples, all the readings showed a cell viability between 90% and 120%. For day 5, all the samples presented a cell viability higher than 100% showing that the metal material samples promoted cell growth. Non-polished samples presented a greater cell viability than polish samples. Metal material having an average grain size of 9 µm showed the greatest viability on non-polished samples.

Example 6—Antibiotic Property of Type 304
Stainless Steel on *Escherichia coli*,
Multidrug-Resistant *Escherichia coli*,
Methicillin-Resistant *Staphylococcus aureus*,
*Staphylococcus Epidermidis* Bacteria
Colony-Forming Unit Normalized to Surface Area in Relationship of Average Grain Size Methods
Type 304 stainless steel material with average crystal grain sizes of 0.5, 1.5, 2, 3 and 9 µm were used in this example.

To ensure there is no contamination samples were washed by sonication three times for 10 minutes with acetone followed by 70% ethanol, and DI water.

Samples were then placed individually into the wells of a 24-well plate and sterilized under UV light overnight. Before cell seeding, samples were rinsed twice with PBS to remove any possible debris. 0.5 mL of the prepared bacteria suspensions ($10^6$ cells/mL) were then added onto each sample and the plates were placed into a stationary incubator maintained at 37° C. and 5% $CO_2$. After 24 h of incubation, the plate was removed from the incubator. The inoculum from each well was aspirated and replaced with 1 ml of PBS. Wells of a sterile 24-well plate were filled with 1 ml of PBS and the samples were transferred to the plate. Samples were washed with PBS three additional times (total 4 PBS rinses). The final PBS wash was not aspirated. Plates were sonicated for 15 min in a chilled water bath.

The plates were vortexed briefly, 10 µl of the solution was pipetted in triplicate onto an agar plate. This stock (0-dilution) was then diluted 1:10, 1:100, 1:1000, 1:10000, and 1:100000 in PBS and each dilution was pipetted onto agar plates. Colony forming units (CFU) were then counted manually after ~12-14 h of incubation.

In the method used in this example, samples were washed (1+3 times) four times to get rid of planktonic cells, these cells are not attached to the samples and are free floating. The samples are washed carefully to do not disrupt the sessile bacteria. The sonication for 15 minutes allowed for the detachment of the bacteria from surface. With counting sessile bacteria allowed for the assessment of the biofilm forming bacteria and biofilm prevention on the surface of sample. It should be appreciated that bacteria can attach to the sample surface and cause infection and biofilm formation is the characteristic of that infection.

Figure 9:
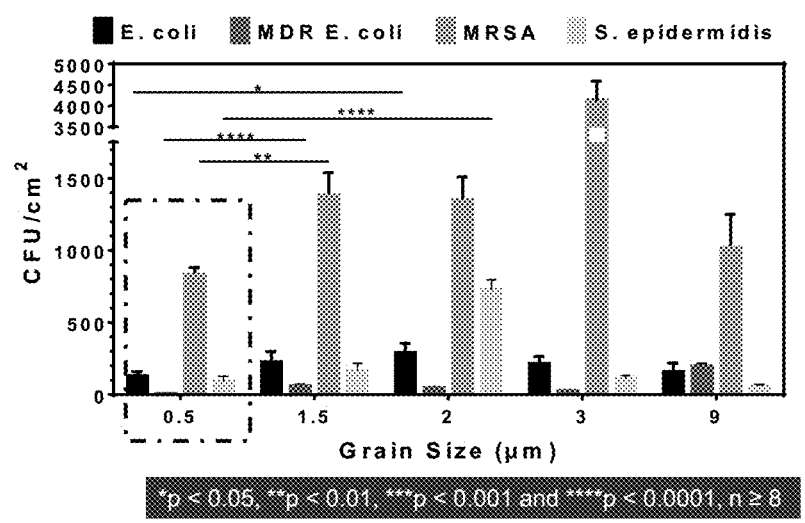
FIG. 9 is an example of a response profile obtained by plotting a response amount (CFU/cm$^2$) normalized to surface area of four bacterial strains *E. coli*, MDR *E. coli*, MRSA and *S. epidermidis* with respect to an average crystal grain size of type 304 stainless steel according to some embodiments.

Results
FIG. 9 shows that decreasing the average crystal grainsize to 0.5 µm causes decrease in bacteria adhesion to the surfaces of the metal material for all of the tested strains of bacteria. The tested bacteria include gram-negative and gram-positive bacteria, drug resistant and drug sensitive bacteria). This decrease was more noticeable in case of Multidrug-Resistant *Escherichia coli* (MDR *E. coli*) Bacterium. Growth of MDR *E. coli* was inhibited by magnitude of 4-49 times for the average grain size to 0.5 µm compare to other grain size.

Example 7-Biofilm Formation Test Using Safranin

Methods
To ensure there is no contamination samples were washed by sonication three times for 10 minutes with acetone followed by 70% ethanol, and DI water. Samples were then placed individually into the wells of a 24-well plate and sterilized under UV light overnight. Before cell seeding, samples were rinsed twice with PBS to remove any possible debris. 0.5 mL of the prepared bacteria suspensions ($10^6$ cells/mL) were then added onto each sample and the plates were placed into a stationary incubator maintained at 37° C. and 5% $CO_2$. After 24 h of incubation, the plate was removed from the incubator. The inoculum was aspirated from each well and replaced with 1 ml of PBS. The wells of a sterile 24-well plate were filled with 1 ml of PBS and the samples were transferred to the plate. The wells were washed with PBS three additional times (total 4 PBS rinses).

The samples were stained with safranin (0.1% w/v) for 5 min. Safranin is a cationic dye used in histology and cytology to distinguish and identify different tissues and cells. Safranin is used to stain gram-positive and gram-negative bacteria.

The samples were washed using 1 ml of PBS 3-4 times (until the PBS is color less).

Figure 13:
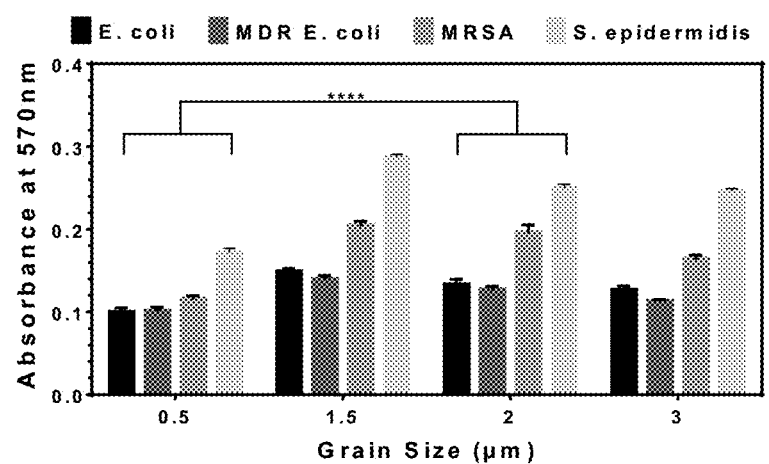
FIG. 13 shows a response profile of biofilm formation using safranin by plotting absorbance at 570 nm with respect to an average crystal grain size of type 304 stainless steel according to some embodiments.

The safranin was resolubilized using 95% ethanol. The absorbance of resolubilized safranin from each well was measured using a spectrophotometer (SpectraMax M3, Molecular Devices, Sunnyvale, Calif.) with $\lambda_{ab}$, the wavelength of absorbance, set to 570 nm Results
FIG. 13 shows that decreasing the average crystal grain size to 0.5 µm causes reduction in biofilm formation on the surfaces of the samples for all of the tested strains of bacteria. Tested bacteria are including gram-negative and gram-positive bacteria, drug resistant and drug sensitive bacteria.

It should be appreciated that the biofilm formation process comprises three steps:
1—Adsorption, or the accumulation of an organism on a collector surface i.e. substrate or sample.
2—Attachment, or the consolidation of the interface between an organism and a collector, often involving the formation of polymer bridges between the organism and collector.
3—Colonization, or growth and division of organisms on the collector's surface. (see Garrett, T. R., Bhakoo, M. and Zhang, Z., 2008. Bacterial adhesion and biofilms on surfaces. Progress in Natural Science, 18(9), pp. 1049-1056.)

Biofilm prevention percentage for 0.5 μm samples was calculated compare to other grainsizes (i.e. 1.5, 2, 3 μm):

In case of *E. coli*, a 21-34% biofilm prevention was observed as compared to the 1.5, 2, 3 μm average crystal grain size samples.

In case of MDR *E. coli*, a 10-28% biofilm prevention was observed as compared to the 1.5, 2, 3 μm average crystal grain size samples.

In case of MRSA, a 29-44% biofilm prevention was observed as compared to the 1.5, 2, 3 μm average crystal grain size samples.

In case of *S. epidermidis*, a 30-41% biofilm prevention was observed as compared to the 1.5, 2, 3 μm average crystal grain size samples.

Example 8—Effect of Grain Size Fibroblast Growth

The cytotoxicity of the metal material on Human Dermal Fibroblast (HDF) (ATCC® CCL-110™) was investigated.

Methods

First, Human Dermal Fibroblast cells were cultured in complete media (Eagle's Minimum Essential (EMEM) medium with 10% fetal bovine serum and 1% penicillin streptomycin) separately in a flask at 37° C. in a humidified incubator with 5% $CO_2$.

Then, the cells were seeded in a 48-well plate with the metal wire samples at 5,000 cells/well in 1000 μL of cell medium, and incubated for 3, 5, and 7 days at 37° C. in a 5% $CO_2$ humidified atmosphere.

After the incubation period of time, the culture media was removed and replaced with 1000 μL of an MTS solution at 1:5 dilution in fresh media (200 μL+1000 μL EMEM). This time, the well plate was cultivated for just 3 hours to allow for a color change. Absorbance was measured at 490 nm under an absorbance plate reader (SpectraMax). Data were expressed as percentage of cell viability.

The metal samples tested were type 316 stainless steel and type 304 stainless steel wires having different diameters and average different grain sizes as shown below:

Type 304 stainless steel samples: The metal samples tested were type 304 stainless steel wires having different diameters (φ in mm) and different average grain sizes (in μm).

CG304 φ0.8 grain size 21.5 μm
CG304 φ0.4 grain size 12.0 μm
CG304 φ0.2 grain size 15.0 μm
UFGSS 304 φ0.8 grain size 0.27 μm
UFGSS 304 φ0.4 grain size 0.22 μm
UFGSS 304 φ0.2 grain size 0.23 μm The chemical composition of the type 304 stainless steel metal samples used is shown in the table below:

TABLE 4

| type | Diameter (mm) | C | Si | Mn | P | S | Ni | Cr | Mo |
|---|---|---|---|---|---|---|---|---|---|
| CG | 0.8 | 0.03 | 0.44 | 1.04 | 0.031 | 0.005 | 9.03 | 18.06 | — |
|  | 0.4 | 0.02 | 0.40 | 1.05 | 0.034 | 0.005 | 10.06 | 18.07 | — |
|  | 0.2 | 0.018 | 0.363 | 1.086 | 0.0341 | 0.0015 | 10.052 | 18.152 | — |
| UFGSS | 0.8 | 0.06 | 0.25 | 1.66 | 0.040 | 0.026 | 8.02 | 18.72 | — |
|  | 0.4 | 0.05 | 0.30 | 1.41 | 0.039 | 0.002 | 9.06 | 18.12 | — |
|  | 0.2 | 0.06 | 0.25 | 1.66 | 0.040 | 0.026 | 8.02 | 18.72 | — |

Type 316 stainless steel samples: The metal samples tested were type 316 stainless steel wires having different diameters (φ in mm) and different average grain sizes (in μm).

CG316 φ0.8 grain size 16.5 μm
CG316 φ0.4 grain size 10.7 μm
CG316 φ0.2 grain size 7.1 μm
UFGSS 316 φ0.8 grain size 0.25 μm
UFGSS 316 φ0.4 grain size 0.22 μm
UFGSS 316 φ0.2 grain size 0.18 μm The chemical composition of the type 316 stainless steel metal samples used is shown in the table below:

TABLE 5

| type | Diameter (mm) | C | Si | Mn | P | S | Ni | Cr | Mo |
|---|---|---|---|---|---|---|---|---|---|
| CG | 0.8 | 0.03 | 0.58 | 1.05 | 0.026 | 0.001 | 12.08 | 17.62 | 2.07 |
|  | 0.4 | 0.040 | 0.50 | 1.04 | 0.029 | 0.001 | 12.10 | 17.44 | 2.02 |
|  | 0.2 | 0.020 | 0.42 | 1.33 | 0.029 | 0.001 | 10.10 | 16.00 | 2.00 |
| UFGSS | 0.8 | 0.03 | 0.39 | 1.04 | 0.027 | 0.001 | 11.56 | 17.38 | 2.03 |
|  | 0.4 | 0.03 | 0.39 | 1.04 | 0.027 | 0.001 | 11.56 | 17.38 | 2.03 |
|  | 0.2 | 0.03 | 0.39 | 1.04 | 0.027 | 0.001 | 11.56 | 17.38 | 2.03 |

The diameters and area samples of the sample tested are shown in table below:

TABLE 6

| Diameter samples (mm) | 0.2 | 0.4 | 0.8 |
|---|---|---|---|
| Area samples (mm$^2$) | 8.04 | 16.21 | 32.92 |

Figure 4A:
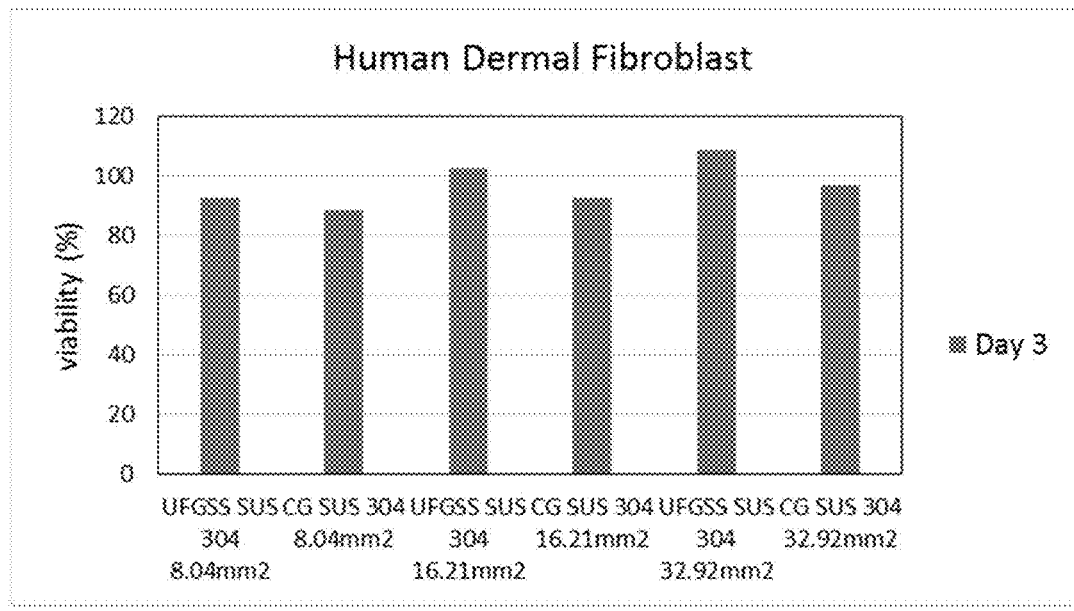
Figure 4B:
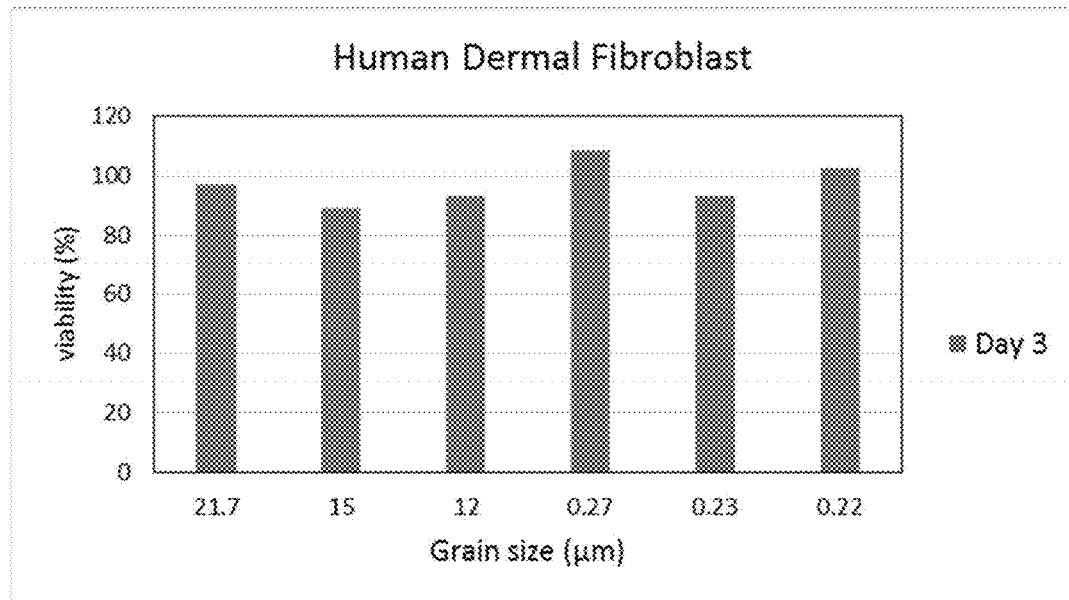

FIGS. 4A-4C show the percent viability of the human dermal fibroblast when grown on type 304 stainless steel metal samples. FIG. 4C showed that average crystal grain size of 0.22 and 0.27 μm for ultrafine type 304 stainless steel metal samples promote human dermal fibroblasts.

Figure 5A:
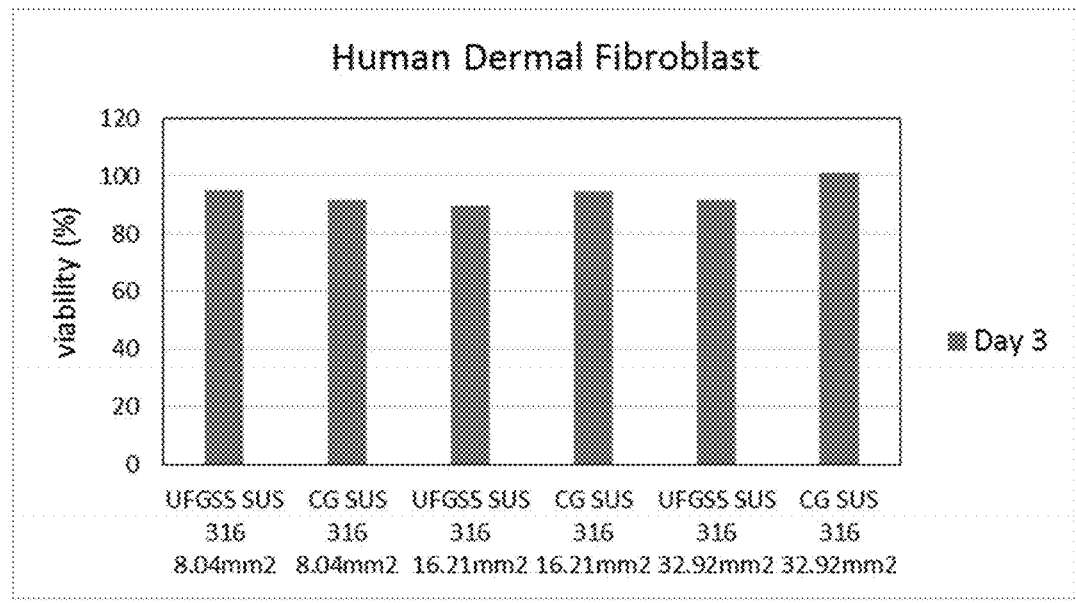
Figure 5B:
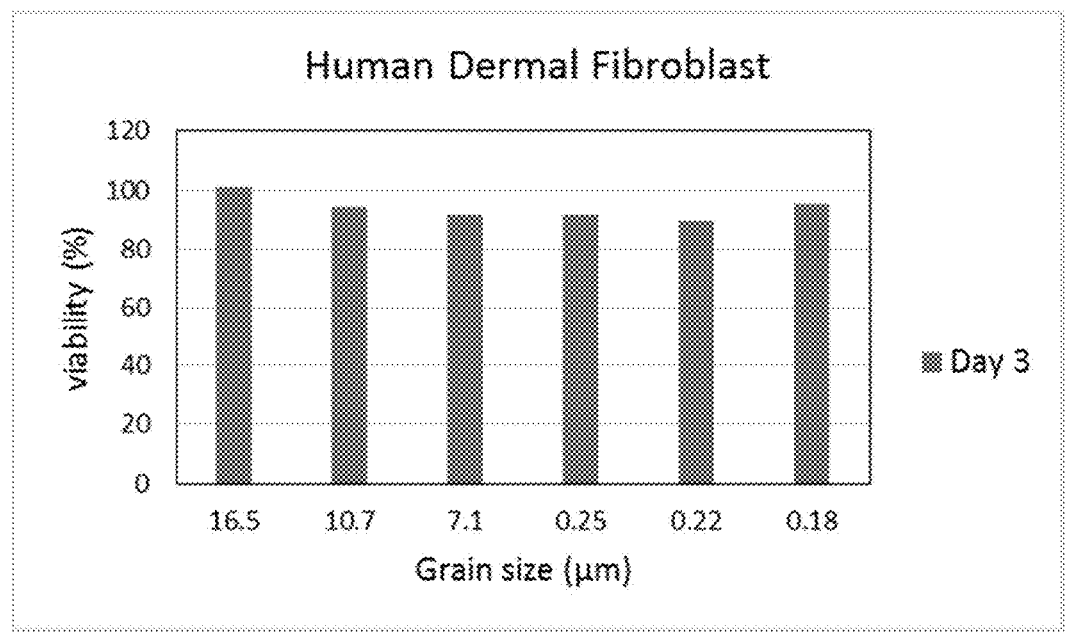

FIGS. 5A-5C show the percent viability of the human dermal fibroblast when grown on type 316 stainless steel metal samples. FIG. 5C showed that average grain size of 16.5 μm, for conventional metal sample, promote human dermal fibroblasts.

Figure 8:
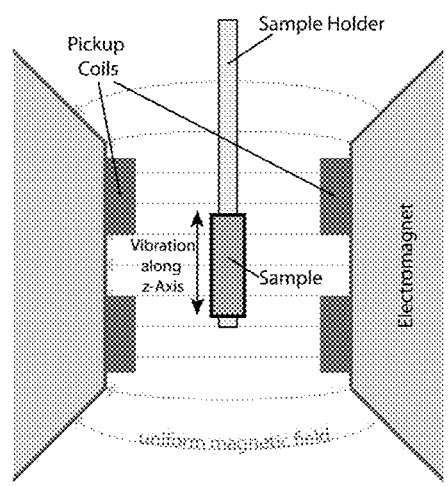
FIG. 8 is a schematic representation of the vibrating-sample magnetometer used for the according to some embodiments.

Example 9: Effect of Magnetic Polarization of Type 304 Stainless Steel and of Grain Size on Bacteria Forming Colonies Methods A vibrating-sample magnetometer (VSM, The LakeShore 7407 VSM) was used to investigate the magnetic susceptibility of the samples (FIG. 8). The sample volume used was equal to 6.2 mm$^3$ and was the same through all the grain sizes tested.

The vibrating-sample magnetometer was used at room temperature to measure the magnetic susceptibility of the type 304 and type 316 stainless steel with various average crystal grain sizes (0.5, 1.5, 2, 3, 9, 10 μm). The specimens were fixed onto sample holder and a magnetic field in the range of −1000 to +1000 oersted (Oe) to measure the magnetic susceptibility of them. (n≥2).

Type 304 stainless steel with different average crystal grain sizes (0.5, 1, and 9, μm) were used in this example.

Samples were magnetized with a 0.1 tesla magnet (0.1 T), 0.5 tesla magnet (0.5 T) and 1.1 tesla magnet (1.1 T).

Results

Figure 10:
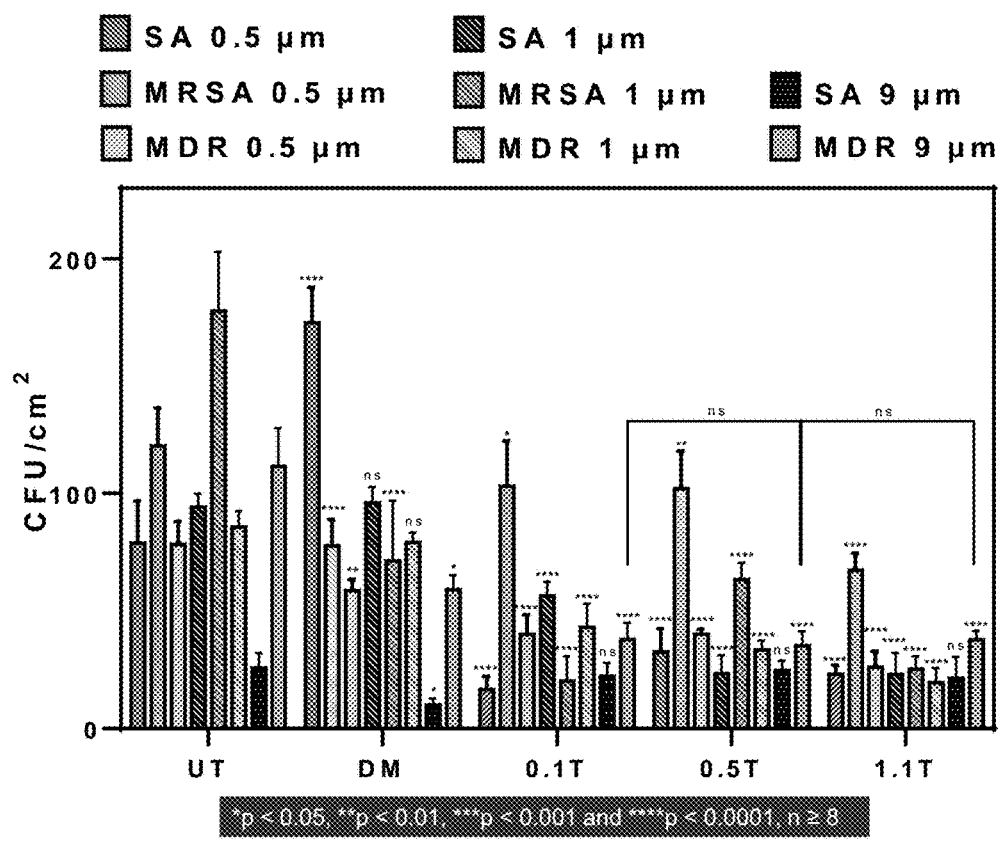
FIG. 10 is an example of a response profile obtained by plotting a response amount (CFU/cm$^2$) normalized to surface area of three bacterial strains MDR *E. coli*, MRSA and *S. aureus* with respect to an average crystal grain size and magnetic properties of type 304 stainless steel sample according to some embodiments.

FIG. 10 shows that controlling the magnetic moment of type 304 stainless steel samples (0.1 T, 0.8 T, 1.1 T) reduced bacteria adhesion to the samples compared to untreated (UT) or demagnetized (DM) type 304 stainless steel samples. Magnetized samples demonstrated more significant decrease in bacteria adhesion. Statistical analysis represents the difference with untreated samples (UT).

Type 304 stainless steel samples with an average crystal grain size of 0.5 and 1 μm demonstrated more reduction in bacteria adhesion/biofilm formation due to their highest magnetic susceptibility as compared to 9 μm grained samples.

Table 7 shows the magnetic moments at 0.1 T

| 304 Grainsize (μm) | Magnetic moment at 0.1 T (memu) |
|---|---|
| 0.5 | 144.98 ± 8.90 |
| 1.5 | 6.75 ± 0.070 |
| 2 | 5.85 ± 0.070 |
| 3 | 5.25 ± 0.70 |
| 9 | 4.6 ± 0.01 |

Table 7 shows that decreasing the average crystal grain size increases the magnetic susceptibility of the type 304 stainless steel samples and that type 304 stainless steel samples with an average crystal grain size of 0.5 μm demonstrated highest magenta susceptibility, above 144.98±8.90 memu.

Example 10—Bone Growth

Methods 26000 human fetal osteoblastic cells (≈2×10$^4$ cells cm$^{-2}$) were seeded per specimen with 500 μL of appropriate culture media with 10% FBS and 1% penicillin-streptomycin inside a 24-well plate that was tissue culture-treated. The plate was left to incubate for 3, 24, and 72 h under static conditions at 37° C. and in an environment enriched with 5% $CO_2$. After the incubation period, the metabolic activity of cells adhered to the surface of each specimen was quantified. Briefly, the overlying media was carefully aspirated and replaced with appropriate media containing 20% MTS reagent. The cells were allowed to incubate with the MTS mixture for 3 h at 37° C. and 5% $CO_2$, in the dark. Post incubation, the absorbance of each well was measured using a spectrophotometer (SpectraMax M3, Molecular Devices, Sunnyvale, Calif.) with $\lambda_{ab}$, the wavelength of absorbance, set to 490 nm. The procured OD data were analysed graphically and statistically. Type 304 stainless steels with different average crystal grain sizes (0.5, 1, and 9 μm) were used in this test.

Results

Figure 11:
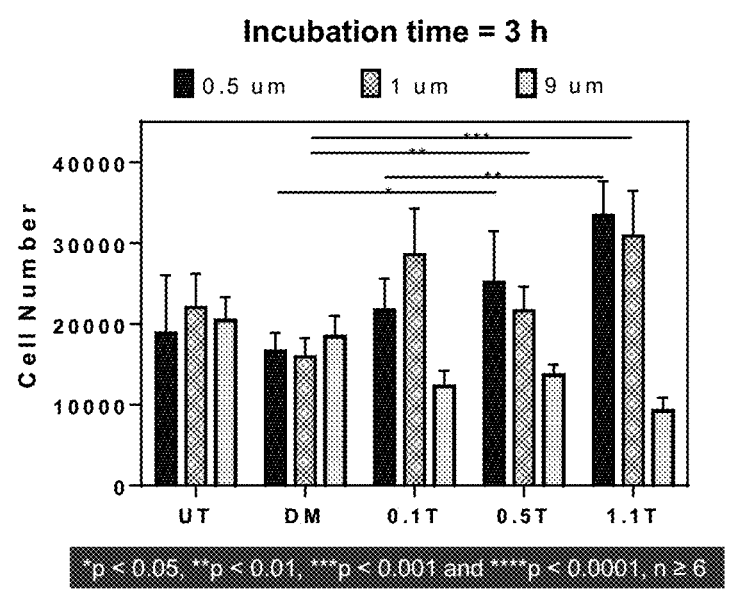
FIG. 11 is an example of a response profile obtained by plotting a response amount (cell number) normalized to surface area of human fetal osteoblast with respect to an average crystal grain size and magnetic properties of type 304 stainless steel sample according to some embodiments.

FIG. 11 shows that the higher number of osteoblasts adhered to the magnetized 304 stainless samples after 3 h post-incubation time. In addition, FIG. 11 shows that magnetization of type 304 stainless samples having an average crystal grain size of 0.5 and 1 μm using a 1.1 T magnet increases cell adhesion while magnetization of type 304 stainless sample having an average crystal grain size of 9 μm does not affect cell adhesion.

Figure 12A:
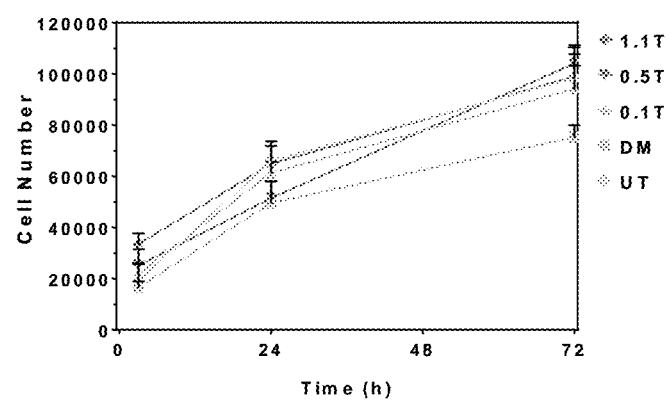
FIGS. 12A-12C are examples of a response profile obtained by plotting a response amount (cell number) normalized to surface area of human fetal osteoblast with respect to an average crystal grain size and magnetic properties of type 304 stainless steel sample according to some embodiments.
Figure 12B:
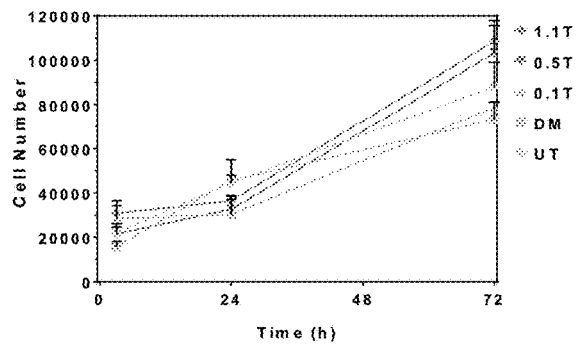
Figure 12C:
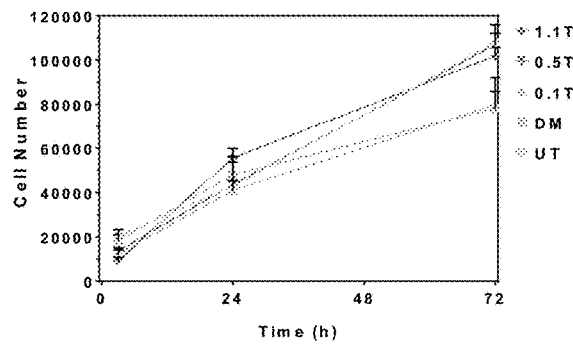

FIGS. 12A-C show that all magnetized type 304 stainless samples having an average crystal grain size of 0.5 μm (FIG. 12A), 1 μm (FIG. 12B) or 9 μm (FIG. 12C) tested support cell adhesion and growth up to 72 hours post-incubation. In addition, FIGS. 12A-C demonstrated the lowest growth on demagnetized (DM) samples at 72 hours post-incubation time.

Example 11: Antibiotic Property of Type 316 Stainless Steel on Bacteria Colony-Forming Unit in Relationship of Average Grain Size, Magnetic Properties, and Surface Energy Methods Methicillin-resistant *Staphylococcus aureus* bacteria (MRSA) were first incubated overnight. After reaching a concentration of 10$^5$, the bacterial were mixed with the metal material samples and incubated for 24 hours. The samples were then washed with distilled water and sonicated for 10 min. After vortexing the samples for an extra 10 seconds, several dilutions of each sample were placed on agar plates. The agar plates were incubated for 12 hours.

Material

The chemical composition of the type 316 stainless steel metal samples used is shown below.

TABLE 9

| material | grain size (μm) | C (W %) | Si (W %) | Mn (W %) | P (W %) | S (W %) | Ni (W %) | Cr (W %) | Mo (W %) |
|---|---|---|---|---|---|---|---|---|---|
| 316 | 10.7 | 0.040 | 0.50 | 1.04 | 0.029 | 0.001 | 12.10 | 17.44 | 2.02 |
|  | 0.22 | 0.03 | 0.39 | 1.04 | 0.027 | 0.001 | 11.56 | 17.38 | 2.03 |

The metal samples tested were type 316 stainless steel wires having diameter φ 0.4 mm and having different grain sizes: ultrafine material with an average grain size of 0.22 μm and conventional material with an average grain size of 10.7 μm.

Samples were placed on the vibrating sample magnetometer (7400-S Series VSN, Lake Shore) sample holder. Readings were set up with a magnetic field range from 5000 Oe to −5000 Oe, Results The results of the response amount (CFU/cm$^2$) with respect to an average crystal grain size of a crystal grain, magnetic properties and surface energy are shown below.

| Average grain size (μm) | Surface energy (mN/m) | Magnetic moment (memu) | CFU/cm$^2$ |
|---|---|---|---|
| 10.7 | 332.14 | 0.92 | 520 |
| 0.22 | 37.39 | 69.39 | 6 |

The CFU/cm$^2$ of MRSA on the type 316 stainless steel metal materials wire was decreased when the average crystal grain size was 0.22 μm (6 CFU/cm$^2$) compared to when the average crystal grain size was 10.7 μm (520 CFU/cm$^2$). The surface energy of the sample was decreased when the average crystal grain size was 0.22 μm (37.39 mN/m) compared to when the average grain size was 10.7 μm (332.14 mN/m). Without being bound to the theory, when the surface energy of the metal sample is close to 42 mN/m, the adhesion of MRSA to the type 316L stainless steel metal materials is decreased. Increase of magnetic moment by work hardening is observed on the type 316 stainless steel metal materials wire having 0.22 μm average crystal grain size compared the conventional type 316 stainless steel wire having 10.7 μm average grain size.

Example 12—Antibiotic Property of Type 316 Stainless Steel on Bacteria Colony-Forming Unit in Relationship of Average Grain Size, Magnetic Properties, and Surface Energy Methods

*P. aeruginosa* were first incubated overnight. After reaching a concentration of 10$^5$, the bacterial were mixed with the metal material samples and incubated for 24 hours. The samples were then washed with distilled water and sonicated for 10 min. After vortexing the samples for an extra 10 seconds, several dilutions of each sample were placed on agar plates. The agar plates were incubated for 12 hours.

Material

The chemical composition of the type 316 stainless steel metal samples used is shown in the table below.

TABLE 10

| material | grain size (μm) | C (W %) | Si (W %) | Mn (W %) | P (W %) | S (W %) | Ni (W %) | Cr (W %) | Mo (W %) |
|---|---|---|---|---|---|---|---|---|---|
| 316 | 16.5 | 0.030 | 0.58 | 1.05 | 0.026 | 0.001 | 12.08 | 17.62 | 2.07 |
|  | 0.25 | 0.03 | 0.39 | 1.04 | 0.027 | 0.001 | 11.56 | 17.38 | 2.03 |

The metal samples tested were type 316 stainless steel wires having diameter φ 0.8 mm, having different grain sizes: ultrafine material sample with an average grain size of 0.25 μm and conventional material sample with an average grain size of 16.5 μm. Samples were placed on the vibrating sample magnetometer (7400-S Series VSN, Lake Shore) sample holder. Readings were set up with a magnetic field range from 5000 Oe to −5000 Oe.

Results

The results of the response amount (CFU/cm$^2$) with respect to an average crystal grain size of a crystal grain, magnetic properties and surface energy are shown below.

| Average grain size (μm) | Surface energy (mN/m) | Magnetic moment (memu) | CFU/cm$^2$ |
|---|---|---|---|
| 16.5 | 971 | 1.20 | 73 |
| 0.25 | 1.87 | 155.73 | 24 |

The CFU/cm$^2$ of *P. aeruginosa* on the type 316 stainless steel metal materials wire was decreased when the average grain size was 0.25 μm (24 CFU/cm$^2$) compared to when the average grain size was 16.5 μm (73 CFU/cm$^2$). The surface energy of the type 316 stainless steel metal materials wire was decreased when the average grain size was 0.25 μm (1.87 mN/m) compared to when the average grain size was 16.5 μm (971 mN/m). Without being bound to the theory, when the surface energy of the metal sample is close to about 42 mN/m, the adhesion of *P. aeruginosa* to the type 316L stainless steel metal materials decreases. Increase of magnetic moment by work hardening is observed on the type 316 stainless steel metal materials wire having 0.25 μm average grain size compared the conventional type 316 stainless steel wire having 16.5 μm average grain size.

Example 13—Antibiotic Property of Type 304 Stainless Steel on Bacteria Colony-Forming Unit in Relationship of Average Grain Size, Magnetic Properties, and Surface Energy Methods MRSA were first incubated overnight. After reaching a concentration of 10$^5$, the bacterial were mixed with the metal material samples and incubated for 24 hours. The samples were then washed with distilled water and sonicated for 10 min. After vortexing the samples for an extra 10 seconds, several dilutions of each sample were placed on gar plates. The agar plates were incubated for 12 hours.

Material

The chemical composition of the type 304 stainless steel metal samples used is shown in the table below.

TABLE 11

| material | grain size (μm) | C (W %) | Si (W %) | Mn (W %) | P (W %) | S (W %) | Ni (W %) | Cr (W %) | Mo (W %) |
|---|---|---|---|---|---|---|---|---|---|
| 304 | 21.5 | 0.03 | 0.44 | 1.04 | 0.031 | 0.005 | 9.03 | 18.06 | — |
|  | 0.27 | 0.06 | 0.25 | 1.66 | 0.040 | 0.026 | 8.02 | 18.72 | — |

The metal samples tested were type 304 stainless steel wires having diameter φ 0.8 mm, having different grain sizes: ultrafine material sample with an average grain size of 0.27 μm and conventional material sample with an average grain size of 21.5 μm.

Samples were placed on the vibrating sample magnetometer (7400-S Series VSN, Lake Shore) sample holder. Readings were set up with a magnetic field range from 5000 Oe to −5000 Oe, Results The results of the response amount (CFU/cm$^2$) with respect to an average crystal grain size of a crystal grain, magnetic properties, and surface energy is shown in the table below.

| Average grain size (μm) | Surface energy (mN/m) | Magnetic moment (memu) | CFU/cm$^2$ |
|---|---|---|---|
| 21.5 | 15.08 | 7.05 | 82 |
| 0.27 | 323.27 | 1084.58 | 23 |

The CFU/cm$^2$ of MRSA on the type 304 stainless steel metal materials wire was decreased when the average grain size was 0.27 μm (23 CFU/cm$^2$) compared to when the average grain size was 21.5 μm (82 CFU/cm$^2$). The surface energy of the type 304 stainless steel metal materials wire was 324.27 mN/m when the average grain size was 0.27 μm compared to 15.08 mN/m when the average grain size was 21.5 μm. Increase of magnetic moment by work hardening is also observed on the type 304 stainless steel metal materials wire having 0.27 μm average grain size compered the conventional type 304 stainless steel wire having 21.5 μm average grain size. Without being bound to the theory, for the type 304 stainless steel metal, when the magnetic moment is increased, the surface energy effect is weaker.

Example 14: Osteoblast Cell Growth Data Using Titanium Alloy

Human Fetal Osteoblast Cells (hFOB) (CRL-11372, ATCC) Cytotoxicity Studies

Human Fetal Osteoblast cells were cultured in complete media (Dulbecco's Modified Eagle Medium (DMEM/F12) with 10% fetal bovine serum and 1% penicillin streptomycin) separately in a flask at 37° C. in a humidified incubator with 5% CO$_2$. Cells were then seeded in a 48-well plate with the wire samples at 5,000 cells/well in 1000 μL of cell medium, and incubated for 3, 5, and 7 days at 37° C. in a 5% CO$_2$ humidified atmosphere. After the incubation period of time, the culture media was removed and replaced with 1000 μL of a PrestoBlue solution at 1:10 dilution in fresh media (100 μL+900 μL DMEM/F12). This time, the well plate was cultured for 45 minutes to allow for a color change. Fluorescence was measured at 560 nm excitation wavelength and 590 nm emission wavelength under a plate reader (SpectraMax). Data were expressed as percentage of cell viability.

Table 12 shows the titanium alloy samples used.

TABLE 12

| Samples (Length 12.7 mm) | Diameter (mm) | Area (mm2) |
|---|---|---|
| Grain size 8.8 μm | 1.7 | 72.37 |
| Grain size 3.1 μm | 1.7 | 72.37 |
| Grain size 2 μm | 1.7 | 72.37 |
| Grain size 1.6 μm | 1.7 | 72.37 |
| Grain size 0.8 μm | 1.7 | 72.37 |
| (*)Control sample 1: Ti6/4Eli | 1.57 | 66.73 |
| (*)Control sample 2: Ti6/4Eli | 1.98 | 85.21 |

(*)Unknown grain size

Table 13 shows the composition of the titanium alloy control samples

TABLE 13

| ASTM F136 Titanium | |
|---|---|
| Nitrogen, max. | 0.05 |
| Carbon, max. | 0.08 |
| Hydrogen, max. | 0.012 |
| Iron, max. | 0.25 |
| Oxygen, max. | 0.13 |
| Aluminum | 5.50-6.50 |
| Vanadium | 3.50-4.50 |
| Titanium | Balance |

Cell Growth Assays Using Human Fetal Osteoblast (hFOB) Cells.

Figure 7:
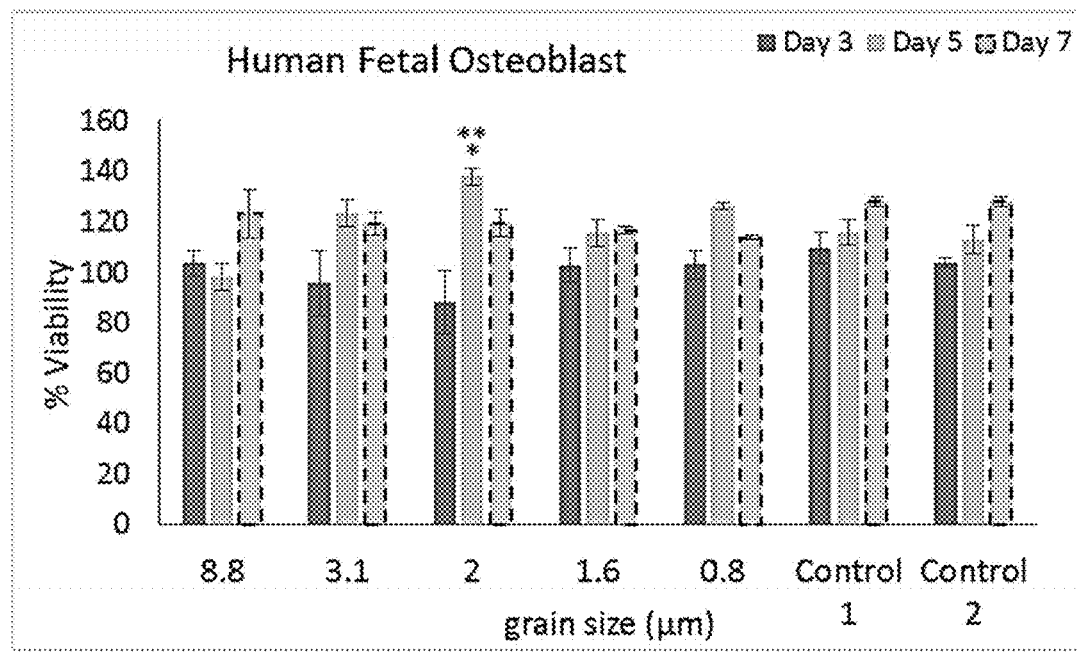
FIG. 7 is a graph showing the percent viability of Human Fetal Osteoblast in cell growth assay on titanium alloy according to some embodiments.

For all samples tested, the percentage of viability was higher than 80%, during the 7 days incubation, showing a relatively low cytotoxicity against hFOB cells (see FIG. 7).

Moreover, the percentage of viability values was higher than 100% in most of the cases, which indicates that a higher number of cells grew in presence of the samples compared with the number of cells that grew in contact with just fresh media. Without being bound to the theory, cells grew on the top of the titanium samples, which promoted their proliferation.

The percentage of cell viability slightly decreased for samples with a grain size of 3.1, 2, and 0.8 μm after day 5.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

What is claimed is:

1. A stainless steel metal material comprising a homogeneous crystal grain nanostructure and having an average crystal grain size from 0.1 to 1 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

2. The stainless steel metal material according to claim 1 comprising a homogeneous crystal grain nanostructure and having an average crystal grain size from 0.2 to 1 μm.

3. The stainless steel metal material according to claim 1 comprising a homogeneous crystal grain nanostructure and having an average crystal grain size from 0.2 to 0.5 μm.

4. The stainless steel metal material according to claim 1, wherein the metal material is 304 stainless steel metal and wherein the material is magnetized.

5. The stainless steel metal material according to claim 1, wherein the metal material is 316 stainless steel metal and wherein the material is magnetized.

6. The stainless steel metal material according to claim 1, wherein the metal material inhibits adsorption or growth of microorganisms on the metal material by at least 50%.

7. The stainless steel metal material according to claim 1, wherein the metal material is magnetized.

8. The stainless steel metal material according to claim 7, wherein the metal material decreases inflammatory cell adsorption or growth, decrease bacterial adsorption or growth, increase osteoblast adsorption or growth, increase endothelial cell adsorption or growth or combinations thereof.

9. The stainless steel metal material according to claim 1, wherein the metal material decreases inflammatory cell adsorption or growth, decrease bacterial adsorption or growth, increase osteoblast adsorption or growth, increase endothelial cell adsorption or growth or combinations thereof.

10. The stainless steel metal material according to claim 1, wherein the microorganism is a gram positive bacterium.

11. The stainless steel metal material according to claim 1, wherein the microorganism is a gram negative bacterium.

12. The stainless steel metal material according to claim 1, wherein the microorganism is one of Staphylococcus aureus, *Staphylococcus epidermidis*, Methicillin-resistant *Staphylococcus aureus* (MRSA), *E. coli*, Multi-drug resistant *E. coli*, and/or *Pseudomanas aeruginosa*.

13. A 304 stainless steel metal material comprising a homogeneous crystal grain nanostructure and having an average crystal grain size from 0.2 to 0.5 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

14. A 316 stainless steel metal material comprising a homogeneous crystal grain nanostructure and having an average crystal grain size from 0.2 to 0.5 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

15. A wire or a rod made from the stainless steel metal material according to claim 1.

16. A medical device made from the stainless steel metal material according to claim 1.

17. A foil made from the stainless steel metal material according to claim 1.

18. An instrument made from the stainless steel metal material according to claim 1.

19. A kitchenware made from the stainless steel metal material according to claim 1.

20. A wire or a rod made from a stainless steel metal material comprising a homogeneous crystal grain nanostructure and having an average crystal grain size from 0.2 to 0.5 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

21. The wire or rod of claim 20, wherein the metal material is 304 stainless steel metal and wherein the material is magnetized.

22. The wire or rod of claim 20, wherein the metal material is 316 stainless steel metal and wherein the material is magnetized.

23. A medical device made from a stainless steel metal material comprising a homogeneous crystal grain nanostructure and having an average crystal grain size from 0.2 to 0.5 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

24. The medical device of claim 23, wherein the metal material is 304 stainless steel metal and wherein the material is magnetized.

25. The medical device of claim 23, wherein the metal material is 316 stainless steel metal and wherein the material is magnetized.

26. A foil made from a stainless steel metal material comprising a homogeneous crystal grain nanostructure and having an average crystal grain size from 0.2 to 0.5 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

27. The foil of claim 26, wherein the metal material is 304 stainless steel metal and wherein the material is magnetized.

28. The foil of claim 26, wherein the metal material is 316 stainless steel metal and wherein the material is magnetized.

29. An instrument made from a stainless steel metal material comprising a homogeneous crystal grain nanostructure and having an average crystal grain size from 0.2 to 0.5 μm configured (i) to inhibit adhesion, growth or combination thereof of microorganisms, (ii) to promote adhesion, growth or combination thereof of predetermined eukaryotic cells, or (iii) to inhibit adhesion, growth or combination thereof of predetermined eukaryotic cells.

30. The instrument of claim 29, wherein the metal material is 304 stainless steel metal and wherein the material is magnetized.

31. The instrument of claim 29, wherein the metal material is 316 stainless steel metal and wherein the material is magnetized.

32. A stainless steel metal wire comprising a homogeneous crystal grain nanostructure and having an average crystal grain size from 0.2 to 0.5 μm, wherein the metal wire has antibiotic properties.

33. The metal wire of claim 32, wherein the metal material is 304 stainless steel metal and wherein the material is magnetized.

34. The metal wire of claim 32, wherein the metal material is 316 stainless steel metal and wherein the material is magnetized.

35. A stainless steel medical device comprising a homogeneous crystal grain nanostructure and having an average crystal grain size from 0.2 to 0.5 μm, wherein the medical device has antibiotic properties.

36. The metal device of claim 35, wherein the metal material is 304 stainless steel metal and wherein the material is magnetized.

37. The metal device of claim 35, wherein the metal material is 316 stainless steel metal and wherein the material is magnetized.

38. The medical device according to claim 35, wherein the medical device inhibits adsorption or growth of microorganisms on the medical device by at least 50%.

* * * * *